(12) United States Patent
Hanaki et al.

(10) Patent No.: US 12,268,092 B2
(45) Date of Patent: Apr. 1, 2025

(54) PHOTOELECTRIC CONVERSION ELEMENT, IMAGING ELEMENT, OPTICAL SENSOR, MATERIAL FOR PHOTOELECTRIC CONVERSION ELEMENT, AND COMPOUND

(71) Applicant: FUJIFILM Corporation, Tokyo (JP)

(72) Inventors: Naoyuki Hanaki, Kanagawa (JP); Tomoaki Yoshioka, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 437 days.

(21) Appl. No.: 17/736,987

(22) Filed: May 4, 2022

(65) Prior Publication Data

US 2022/0271238 A1    Aug. 25, 2022

Related U.S. Application Data

(63) Continuation of application No. PCT/JP2020/037518, filed on Oct. 2, 2020.

(30) Foreign Application Priority Data

Nov. 8, 2019 (JP) .................................. 2019-203259

(51) Int. Cl.
*C07D 493/04* (2006.01)
*C07D 495/04* (2006.01)
(Continued)

(52) U.S. Cl.
CPC ....... *H10K 85/6576* (2023.02); *C07D 493/04* (2013.01); *C07D 495/04* (2013.01);
(Continued)

(58) Field of Classification Search
CPC .... C07F 9/5325; H10K 85/622; H10K 50/165
(Continued)

(56) References Cited

U.S. PATENT DOCUMENTS 9,806,271 B2 * 10/2017 Lee .......................... H05B 33/22
9,847,491 B2 * 12/2017 Hwang ................ H10K 85/633
(Continued)

FOREIGN PATENT DOCUMENTS

EP        2301921        3/2011
JP      2015149397       8/2015
(Continued)

OTHER PUBLICATIONS

"International Search Report (Form PCT/ISA/210) of PCT/JP2020/037518," mailed on Dec. 22, 2020, with English translation thereof, pp. 1-5.
(Continued)

*Primary Examiner* — Vu A Vu
(74) *Attorney, Agent, or Firm* — JCIPRNET

(57) ABSTRACT

The present invention is to provide a photoelectric conversion element having an excellent photoelectric conversion efficiency and responsiveness after heating over time. In addition, the present invention is to provide an imaging element, an optical sensor, a material for a photoelectric conversion element, and a compound. The photoelectric conversion element of the present invention includes a conductive film, a photoelectric conversion film, and a transparent conductive film in this order, in which the photoelectric conversion film contains a compound represented by Formula (1) and an n-type semiconductor material.

18 Claims, 2 Drawing Sheets

(51) Int. Cl.
  *H10K 85/60* (2023.01)
  *H10K 30/00* (2023.01)
  *H10K 39/32* (2023.01)
(52) U.S. Cl.
  CPC ....... *H10K 85/626* (2023.02); *H10K 85/6574* (2023.02); *H10K 30/00* (2023.02); *H10K 39/32* (2023.02)
(58) Field of Classification Search
  USPC .......................................................... 257/40
  See application file for complete search history.

(56) References Cited

U.S. PATENT DOCUMENTS

| | | | | |
|---|---|---|---|---|
| 9,896,621 | B2* | 2/2018 | Kim | H10K 85/6572 |
| 10,608,049 | B2 | 3/2020 | Murata et al. | |
| 11,133,470 | B2* | 9/2021 | Suganuma | H10K 85/636 |
| 11,183,643 | B2* | 11/2021 | Zhang | C07D 403/04 |
| 11,456,428 | B2* | 9/2022 | Joo | H10K 85/658 |
| 11,502,261 | B2* | 11/2022 | Hong | H10K 85/40 |
| 11,667,647 | B2* | 6/2023 | Bae | H10K 85/631 |
| | | | | 428/690 |
| 2016/0343958 | A1* | 11/2016 | Hirai | H10K 85/655 |
| 2017/0092433 | A1* | 3/2017 | Kanei | H10K 30/353 |
| 2018/0122585 | A1 | 5/2018 | Satou et al. | |
| 2020/0119100 | A1 | 4/2020 | Murata et al. | |

FOREIGN PATENT DOCUMENTS

| | | |
|---|---|---|
| WO | 2009148062 | 12/2009 |
| WO | 2011093309 | 8/2011 |
| WO | 2017002645 | 1/2017 |
| WO | 2017014146 | 1/2017 |

OTHER PUBLICATIONS

"Written Opinion of the International Searching Authority (Form PCT/ISA/237) of PCT/ JP2020/037518," mailed on Dec. 22, 2020, with English translation thereof, pp. 1-8.

"Office Action of Japan Counterpart Application", issued on Jun. 6, 2023, with English translation thereof, p.1-p. 6.

* cited by examiner

PHOTOELECTRIC CONVERSION ELEMENT, IMAGING ELEMENT, OPTICAL SENSOR, MATERIAL FOR PHOTOELECTRIC CONVERSION ELEMENT, AND COMPOUND

CROSS-REFERENCE TO RELATED APPLICATIONS

This application is a Continuation of PCT International Application No. PCT/JP2020/037518 filed on Oct. 2, 2020, which claims priority under 35 U.S.C. § 119(a) to Japanese Patent Application No. 2019-203259 filed on Nov. 8, 2019. The above application is hereby expressly incorporated by reference, in its entirety, into the present application.

BACKGROUND OF THE INVENTION

1. Field of the Invention

The present invention relates to a photoelectric conversion element, an imaging element, an optical sensor, a material for a photoelectric conversion element, and a compound.

2. Description of the Related Art

In recent years, the development of an element (for example, an imaging element) having a photoelectric conversion film has been progressing.

For example, it is disclosed and described in WO2009/148062A that a polycyclic compound has a specific structure, and the polycyclic compound is useful for an organic solar cell or the like ([Claim 1], paragraph [0010], and the like).

SUMMARY OF THE INVENTION

In recent years, along with the demand for improving the performance of imaging elements, optical sensors, and the like, further improvements are required for various characteristics required for photoelectric conversion elements used therein.

For example, further improvements are required for a photoelectric conversion efficiency in the photoelectric conversion elements.

Regarding the photoelectric conversion elements, from manufacturing and/or practical requirements for products or the like on which photoelectric conversion elements are mounted, it is also required that the photoelectric conversion elements can exhibit good responsiveness even after being placed at a high temperature for a certain period of time (hereinafter, the responsiveness of the photoelectric conversion elements after being placed at a high temperature for a certain period of time is referred to as "responsiveness after heating over time").

The present inventors have studied a photoelectric conversion element using materials disclosed in WO2009/148062A, and it was confirmed that there is room for improvement in the photoelectric conversion efficiency and the responsiveness after heating over time in such a photoelectric conversion element.

In view of the above circumstances, the present invention is to provide a photoelectric conversion element that is excellent in a photoelectric conversion efficiency and responsiveness after heating over time.

In addition, the present invention is to provide an imaging element, an optical sensor, a material for a photoelectric conversion element, and a compound.

The present inventors have conducted extensive studies on the above-described problems, and as a result, the inventors have found that it is possible to solve the above-described problems by configurations described below and have completed the present invention.

A photoelectric conversion element comprising, in the following order: a conductive film; a photoelectric conversion film; and a transparent conductive film, in which the photoelectric conversion film contains a compound represented by Formula (1) and an n-type semiconductor material,

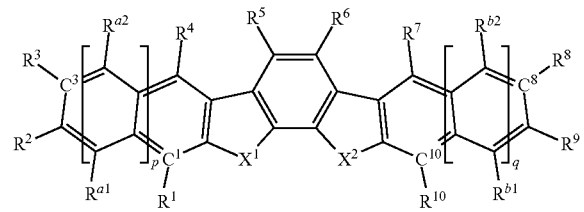

(1)

in Formula (1), $C^1$, $C^3$, $C^8$, and $C^{10}$ each represent a carbon atom, $X^1$ and $X^2$ each independently represent a sulfur atom, an oxygen atom, a selenium atom, a tellurium atom, $CR^{c1}R^{c2}$, $SiR^{c3}R^{c4}$, or $NR^{c5}$, $R^{c1}$ to $R^{c5}$ each independently represent a hydrogen atom or a substituent, p and q each independently represent an integer of 0 to 2, $R^5$ and $R^6$ each independently represent a hydrogen atom or a substituent, and $R^1$ to $R^4$, $R^7$ to $R^{10}$, $R^{a1}$, $R^{a2}$, $R^{b1}$, and $R^{b2}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent, where, in a case where $R^1$ is a heteroaryl group which may have a substituent, an atom directly bonded to $C^1$ in $R^1$, which may have a substituent and is a heteroaryl group, is a carbon atom, in a case where $R^3$ is a heteroaryl group which may have a substituent, an atom directly bonded to $C^3$ in $R^3$, which may have a substituent and is a heteroaryl group, is a carbon atom, in a case where $R^8$ is a heteroaryl group which may have a substituent, an atom directly bonded to $C^8$ in $R^8$, which may have a substituent and is a heteroaryl group, is a carbon atom, and in a case where $R^{10}$ is a heteroaryl group which may have a substituent, an atom directly bonded to $C^{10}$ in $R^{10}$, which may have a substituent and is a heteroaryl group, is a carbon atom.

[2] The photoelectric conversion element according to [1], in which $X^1$ and $X^2$ each independently represent a sulfur atom, an oxygen atom, or a selenium atom.

[3]
The photoelectric conversion element according to [1] or [2], in which at least one of $R^1$ to $R^{10}$, $R^{a1}$, $R^{a2}$, $R^{b1}$, or $R^{b2}$ represents an aryl group which may have a substituent or a heteroaryl group which may have a substituent.

[4]
The photoelectric conversion element according to any one of [1] to [3], wherein the compound represented by Formula (1) is a compound represented by Formula (2),

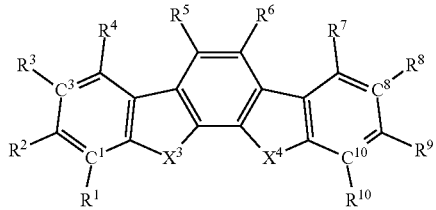

(2)

in Formula (2), $C^1$, $C^3$, $C^8$, and $C^{10}$ each represent a carbon atom, $X^3$ and $X^4$ each independently represent a sulfur atom or an oxygen atom, $R^5$ and $R^6$ each independently represent a hydrogen atom or a substituent, $R^1$ to $R^4$ and $R^7$ to $R^{10}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent, and Formula (2) satisfies at least one of a requirement A or a requirement B, requirement A: $R^2$ and $R^9$ each independently representing an aryl group which may have a substituent or a heteroaryl group which may have a substituent, and requirement B: $R^3$ and $R^8$ each independently representing an aryl group which may have a substituent or a heteroaryl group which may have a substituent, where, in a case where $R^1$ is a heteroaryl group which may have a substituent, an atom directly bonded to $C^1$ in $R^1$, which may have a substituent and is a heteroaryl group, is a carbon atom, in a case where $R^3$ is a heteroaryl group which may have a substituent, an atom directly bonded to $C^3$ in $R^3$, which may have a substituent and is a heteroaryl group, is a carbon atom, in a case where $R^8$ is a heteroaryl group which may have a substituent, an atom directly bonded to $C^8$ in $R^8$, which may have a substituent and is a heteroaryl group, is a carbon atom, and in a case where $R^{10}$ is a heteroaryl group which may have a substituent, an atom directly bonded to $C^{10}$ in $R^{10}$, which may have a substituent and is a heteroaryl group, is a carbon atom.

[5]
The photoelectric conversion element according to [4], in which $X^3$ and $X^4$ each represent a sulfur atom.

[6]
The photoelectric conversion element according to any one of [1] to [5], in which $R^2$ and $R^9$ each independently represent a polycyclic aryl group which may have a substituent, a polycyclic heteroaryl group which may have a substituent, or a group represented by Formula (W-1),

(W-1)

in Formula (W-1),*represents a bonding position, $Ar^1$ represents a monocyclic aromatic ring group which may have a substituent, $Ar^2$ represents an aromatic ring group which may have a substituent, r represents 0 or 1, $L^1$ represents a sulfur atom, an oxygen atom, a selenium atom, $SiR^{w1}R^{w2}$, $NR^{w3}$, or $CR^{w4}R^{w5}$, $R^{w1}$ to $R^{w5}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent, and where, in a case where r represents 0, $L^1$ does not exist, and $Ar^1$ and $Ar^2$ are connected only by a single bond specified in Formula (W-1).

[7]
The photoelectric conversion element according to any one of [1] to [6], wherein $R^2$ and $R^9$ each independently represent a polycyclic aryl group with 3 or more rings, which may have a substituent, a polycyclic heteroaryl group which may have a substituent, or a group represented by Formula (W-2),

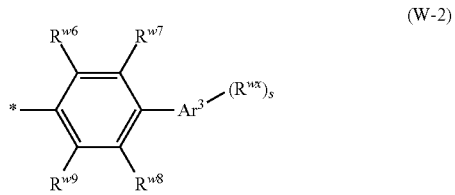

(W-2)

in Formula (W-2),*represents a bonding position, $R^{w6}$ to $R^{w9}$ each independently represent a hydrogen atom, a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent, $Ar^3$ represents a benzene ring group or a polycyclic aromatic heterocyclic group, $R^{wx}$ represents a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent, and s represents an integer of 0 or more.

[8]

The photoelectric conversion element according to any one of [1] to [7], in which the compound represented by Formula (1) has a molecular weight of 400 to 900.

[9]

The photoelectric conversion element according to any one of [1] to [8], in which the photoelectric conversion film has a bulk hetero structure formed in a state where the compound represented by Formula (1) and the n-type semiconductor material are mixed with each other.

[10]

The photoelectric conversion element according to any one of [1] to [9], further comprising one or more interlayers between the conductive film and the transparent conductive film, in addition to the photoelectric conversion film.

[11]

The photoelectric conversion element according to any one of [1] to [10], wherein the n-type semiconductor material includes fullerenes selected from the group consisting of a fullerene and a derivative thereof.

[12]

An imaging element comprising the photoelectric conversion element according to any one of [1] to [11].

[13]

An optical sensor comprising the photoelectric conversion element according to any one of [1] to [11].

[14]

A material for a photoelectric conversion element comprising a compound represented by Formula (3).

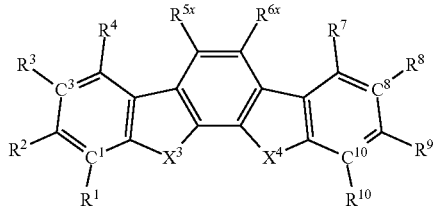

(3)

in Formula (3), $C^1$, $C^3$, $C^8$, and $C^{10}$ each represent a carbon atom, $X^3$ and $X^4$ each independently represent a sulfur atom or an oxygen atom, $R^1$ to $R^4$, $R^7$ to $R^{10}$, $R^{5x}$, and $R^{6x}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent, and Formula (3) satisfies at least one of a requirement A or a requirement B, requirement A: $R^2$ and $R^9$ each independently representing an aryl group which may have a substituent or a heteroaryl group which may have a substituent, and requirement B: $R^3$ and $R^8$ each independently representing an aryl group which may have a substituent or a heteroaryl group which may have a substituent, where, in a case where $R^1$ is a heteroaryl group which may have a substituent, an atom directly bonded to $C^1$ in $R^1$, which may have a substituent and is a heteroaryl group, is a carbon atom, in a case where $R^3$ is a heteroaryl group which may have a substituent, an atom directly bonded to $C^3$ in $R^3$, which may have a substituent and is a heteroaryl group, is a carbon atom, in a case where $R^8$ is a heteroaryl group which may have a substituent, an atom directly bonded to $C^8$ in $R^8$, which may have a substituent and is a heteroaryl group, is a carbon atom, and in a case where $R^{10}$ is a heteroaryl group which may have a substituent, an atom directly bonded to $C^{10}$ in $R^{10}$, which may have a substituent and is a heteroaryl group, is a carbon atom.

[15]

A compound represented by Formula (4),

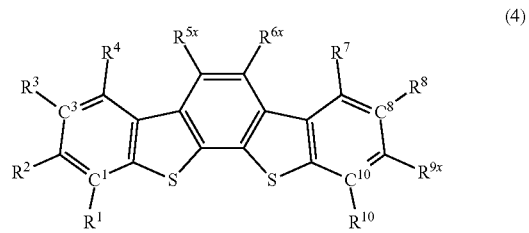

(4)

in Formula (4), $C^1$, $C^3$, $C^8$, and $C^{10}$ each represent a carbon atom, $R^1$, $R^3$, $R^4$, $R^7$, $R^8$, $R^{10}$, $R^{5X}$, and $R^{6X}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent, where, in a case where $R^1$ is a heteroaryl group which may have a substituent, an atom directly bonded to $C^1$ in $R^1$, which may have a substituent and is a heteroaryl group, is a carbon atom, in a case where $R^3$ is a heteroaryl group which may have a substituent, an atom directly bonded to $C^3$ in $R^3$, which may have a substituent and is a heteroaryl group, is a carbon atom, in a case where $R^8$ is a heteroaryl group which may have a substituent, an atom directly bonded to $C^8$ in $R^8$, which may have a substituent and is a heteroaryl group, is a carbon atom, and in a case where $R^{10}$ is a heteroaryl group which may have a substituent, an atom directly bonded to $C^{10}$ in $R^{10}$, which may have a substituent and is a heteroaryl group, is a carbon atom.

$R^{2x}$ and $R^{9X}$ each independently represent a polycyclic aryl group with 3 or more rings, which may have a substituent, a polycyclic heteroaryl group which may have a substituent, or a group represented by Formula (W-2),

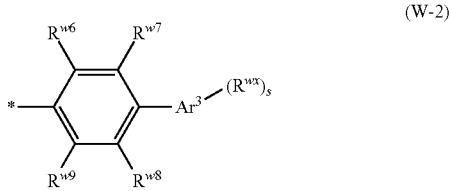

(W-2)

in Formula (W-2),* represents a bonding position, $R^{w6}$ to $R^{w9}$ each independently represent a hydrogen atom, a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent, $Ar^3$ represents a benzene ring group or a polycyclic aromatic heterocyclic group, $R^{wx}$ represents a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent, and s represents an integer of 0 or more.

According to the present invention, it is possible is to provide the photoelectric conversion element having an excellent photoelectric conversion efficiency and responsiveness after heating over time.

In addition, according to the present invention, it is possible to provide the imaging element, the optical sensor, the material for a photoelectric conversion element, and the compound.

DESCRIPTION OF THE PREFERRED EMBODIMENTS

Figure 1:
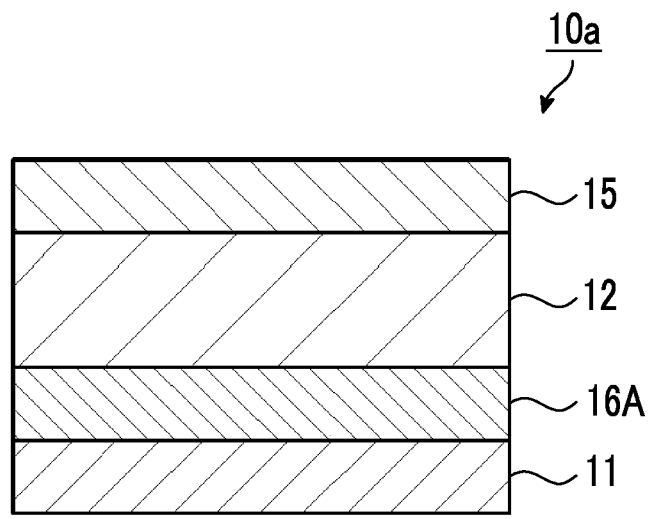
FIG. 1 is a schematic cross-sectional view illustrating a configuration example of a photoelectric conversion element.

Hereinafter, suitable embodiments of a photoelectric conversion element of the present invention will be described.

In the present specification, a "substituent" includes a group exemplified by a substituent W described later, unless otherwise specified.

(Substituent W)

A substituent W in the present specification will be described below.

Examples of the substituent W include a halogen atom (such as a fluorine atom, a chlorine atom, a bromine atom, an iodine atom), an alkyl group (including a cycloalkyl group, a bicycloalkyl group, and a tricycloalkyl group), an alkenyl group (including a cycloalkenyl group and a bicycloalkenyl group), an alkynyl group, an aryl group, a heteroaryl group (the heteroaryl group may also be referred to as a heterocyclic group), a cyano group, a hydroxy group, a carboxy group, a nitro group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkyl or an arylsulfonylamino group, a mercapto group, an alkylthio group, an arylthio group, a heterocyclic thio group, a sulfamoyl group, an alkyl or an arylsulfinyl group, an alkyl or an arylsulfonyl group, an acyl group, an aryloxycarbonyl group, an alkoxycarbonyl group, a carbamoyl group, an aryl or a heterocyclic azo group, an imide group, a phosphino group, a phosphinyl group, a phosphinyloxy group, a phosphinylamino group, a phosphono group, a silyl group, a hydrazino group, a ureido group, and a boronate group ($-B(OH)_2$). Each of the above-described groups may further have a substituent (for example, one or more groups of each of the above-described groups), as possible. For example, an alkyl group which may have a substituent is also included as a form of the substituent W.

In addition, in a case where the substituent W has a carbon atom, the number of carbon atoms of the substituent W is, for example, 1 to 20.

The number of atoms other than a hydrogen atom included in the substituent W is, for example, 1 to 30.

In the present specification, examples of the halogen atom include a fluorine atom, a chlorine atom, a bromine atom, and an iodine atom.

In the present specification, unless otherwise specified, the number of carbon atoms of the alkyl group is preferably 1 to 20, more preferably 1 to 10, and even more preferably 1 to 6.

The alkyl group may be any of linear, branched, or cyclic. Examples of the alkyl group include a methyl group, an ethyl group, an n-propyl group, an i-propyl group, an n-butyl group, a t-butyl group, an n-hexyl group, a cyclopentyl group, and the like.

In addition, the alkyl group may be, for example, a cycloalkyl group, a bicycloalkyl group, or a tricycloalkyl group, and may have a cyclic structure thereof as a partial structure.

In the alkyl group which may have a substituent, a substituent which may be contained in the alkyl group is not particularly limited, an example thereof includes the substituent W, and an aryl group (preferably having 6 to 18 carbon atoms, and more preferably having 6 carbon atoms), a heteroaryl group (preferably having 5 to 18 carbon atoms, and more preferably having 5 and 6 carbon atoms), or a halogen atom (preferably a fluorine atom or a chlorine atom) is preferable.

In the present specification, unless otherwise specified, the above-described alkyl group is preferable as an alkyl group moiety in the alkoxy group. The alkyl group moiety in the alkylthio group is preferably the above-described alkyl group.

In the alkoxy group which may have a substituent, the substituent which may be contained in the alkoxy group includes the same examples as the substituent in the alkyl group which may have a substituent. In the alkylthio group which may have a substituent, the substituent which may be contained in the alkylthio group includes the same examples as the substituent in the alkyl group which may have a substituent.

In the present specification, the alkenyl group may be any of linear, branched, or cyclic, unless otherwise specified. The alkenyl group preferably has 2 to 20 carbon atoms. In the alkenyl group which may have a substituent, the substituent which may be contained in the alkenyl group includes the same examples as the substituent in the alkyl group which may have a substituent.

In the present specification, an alkynyl group may be any of linear, branched, or cyclic, unless otherwise specified. The alkynyl group preferably has 2 to 20 carbon atoms. In the alkynyl group which may have a substituent, the substituent which may be contained in the alkynyl group includes the same examples as the substituent in the alkyl group which may have a substituent.

In the present specification, unless otherwise specified, the aryl group is preferably an aryl group having 6 to 18 ring members.

The aryl group may be monocyclic or polycyclic (for example, with 2 to 6 rings).

The aryl group is preferably, for example, a phenyl group, a naphthyl group, an anthryl group, or a phenanthrenyl group.

In the aryl group which may have a substituent, the substituent which may be contained in the aryl group is not particularly limited, and an example thereof includes the substituent W, an alkyl group which may have a substituent (preferably having 1 to 10 carbon atoms) is preferable, and a methyl group is more preferable.

In a case where the aryl group which may have a substituent has a plurality of substituents, the plurality of substituents may be bonded to each other to form a ring. As described above, in the case where the plurality of substituents are bonded to each other to form a ring, for example, the aryl group which may have a substituent, as a whole, may form a fluorenyl group (such as 9,9-dimethylfluorenyl group) which may further have a substituent.

In the present specification, unless otherwise specified, the heteroaryl group is preferably a heteroaryl group having a monocyclic or polycyclic ring structure, which contains a heteroatom such as a nitrogen atom, a sulfur atom, an oxygen atom, a selenium atom, a tellurium atom, a phosphorus atom, a silicon atom, and/or a boron atom.

The number of carbon atoms among the ring member atoms of the above-described heteroaryl group is not particularly limited, but is preferably 3 to 18, and more preferably 3 to 5.

The number of heteroatoms among the ring member atoms of the heteroaryl group is not particularly limited, but is preferably 1 to 10, more preferably 1 to 4, and even more preferably 1 and 2.

The heteroaryl group may be monocyclic or polycyclic (for example, with 2 to 6 rings).

The number of ring members of the heteroaryl group is not particularly limited, but is preferably 5 to 15.

Examples of the above-described heteroaryl group include a furyl group, a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a benzofuryl group, a thienyl group, a benzothienyl group, a dibenzofuryl group, a dibenzothienyl group, a pyrrolyl group, an indolyl group, an imidazopyridinyl group, a carbazolyl group, and the like.

In the heteroaryl group which may have a substituent, the substituent which may be contained in the heteroaryl group is not particularly limited, and an example thereof includes the substituent W.

In a case where the heteroaryl group which may have a substituent has a plurality of substituents, the plurality of substituents may be bonded to each other to form a ring.

In the present specification, unless otherwise specified, examples of a silyl group which may have a substituent include a group represented by $-Si(R^{S1})(R^{S2})(R^{S3})$. $R^{S1}$, $R^{S2}$, and $R^{S3}$ each independently represent a hydrogen atom or a substituent, and preferably represent an alkyl group which may have a substituent, an alkoxy group which may have a substituent, an alkylthio group which may have a substituent, an aryl group which may have a substituent, or a heteroaryl group which may have a substituent.

In addition, in the present specification, the numerical range represented by "to" means a range including numerical values denoted before and after "to" as a lower limit value and an upper limit value.

In the present specification, a hydrogen atom may be a light hydrogen atom (an ordinary hydrogen atom) or a deuterium atom (a double hydrogen atom and the like).

The photoelectric conversion element according to an embodiment of the present invention includes a conductive film, a photoelectric conversion film, and a transparent conductive film in this order, in which the photoelectric conversion film contains a compound represented by Formula (1) (hereinafter, referred to as a "specific compound") and an n-type semiconductor material.

The mechanism capable of solving the above problems by adopting such a configuration of the photoelectric conversion element according to the embodiment of the present invention is not always clear, but the present inventors speculate as follows.

That is, the specific compound has a structure in which five or more specific rings are linearly fused in the central portion as a mother nucleus, and exhibits appropriate crystallinity in a case where the photoelectric conversion film is formed. Therefore, the photoelectric conversion efficiency is good. In addition, it is considered that since the mother nucleus of the specific compound has a linear structure in which five or more specific rings are linearly fused to have an appropriate length, a state of the photoelectric conversion film is less likely to deteriorate due to heating over time, and responsiveness after heating over time is good.

Hereinafter, the case where the photoelectric conversion efficiency of the photoelectric conversion element and/or the responsiveness after heating over time are more excellent is simply referred to as an "effect of the present invention is more excellent".

FIG. 1 is a schematic cross-sectional view of one embodiment of a photoelectric conversion element of the present invention.

A photoelectric conversion element 10a illustrated in FIG. 1 has a configuration in which a conductive film (hereinafter, also referred to as a lower electrode) 11 functioning as a lower electrode, an electron blocking film 16A, a photoelectric conversion film 12 containing the specific compound described later, and a transparent conductive film (hereinafter, also referred to as an upper electrode) 15 functioning as an upper electrode are laminated in this order.

Figure 2:
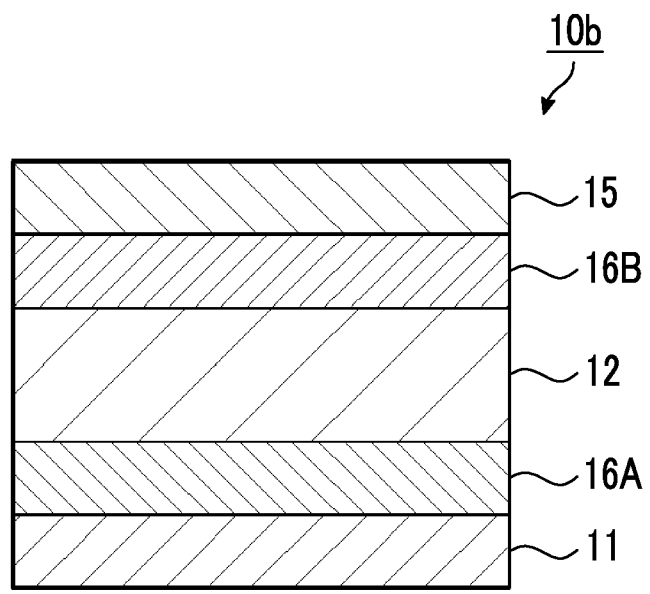
FIG. 2 is a schematic cross-sectional view illustrating a configuration example of the photoelectric conversion element.

FIG. 2 illustrates a configuration example of another photoelectric conversion element. A photoelectric conversion element 10b illustrated in FIG. 2 has a configuration in which the electron blocking film 16A, the photoelectric conversion film 12, a positive hole blocking film 16B, and the upper electrode 15 are laminated on the lower electrode 11 in this order. The lamination order of the electron blocking film 16A, the photoelectric conversion film 12, and the positive hole blocking film 16B in FIGS. 1 and 2 may be appropriately changed according to the application and the characteristics.

In the photoelectric conversion element 10a (or 10b), it is preferable that light is incident on the photoelectric conversion film 12 through the upper electrode 15. In a case where the photoelectric conversion element 10a (or 10b) is used, a voltage can be applied. In this case, it is preferable that the lower electrode 11 and the upper electrode 15 form a pair of electrodes, and a voltage of $1\times10^{-5}$ to $1\times10^{7}$ V/cm is applied between the pair of electrodes. From the viewpoint of the performance and power consumption, the applied voltage is more preferably $1\times10^{-4}$ to $1\times10^{7}$ V/cm, and even more preferably $1\times10^{-3}$ to $5\times10^{6}$ V/cm.

Regarding a voltage application method, in FIGS. 1 and 2, it is preferable that the voltage is applied such that the electron blocking film 16A side is a cathode and the photoelectric conversion film 12 side is an anode. In a case where the photoelectric conversion element 10a (or 10b) is used as an optical sensor, or also in a case where the photoelectric conversion element 10a (or 10b) is incorporated in an imaging element, the voltage can be applied by the same method.

As described in detail below, the photoelectric conversion element 10a (or 10b) can be suitably applied to applications of the imaging element.

Hereinafter, the form of each layer constituting the photoelectric conversion element according to the embodiment of the present invention will be described in detail.

<Photoelectric Conversion Film>

The photoelectric conversion film is a film containing a specific compound.

Hereinafter, the specific compound will be described in detail.

(Compound (Specific Compound) Represented by Formula (1))

The specific compound is a compound represented by Formula (1).

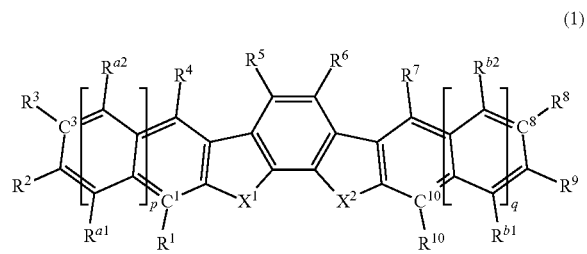

(1)

In Formula (1), $C^1$, $C^3$, $C^8$, and $C^{10}$ each represent a carbon atom.

In Formula (1), $X^1$ and $X^2$ each independently represent a sulfur atom (—S—), an oxygen atom (—O—), a selenium atom (—Se—), a tellurium atom (—Te—), $CR^{c1}R^{c2}$ (—$CR^{c1}R^{c2}$—), $SiR^{c3}R^{c4}$ (—$SiR^{c3}R^{c4}$—), or $NR^{c5}$ (—$NR^{c5}$—).

$X^1$ and $X^2$ are each independently preferably a sulfur atom, an oxygen atom, or a selenium atom, more preferably a sulfur atom or an oxygen atom, and even more preferably a sulfur atom.

$R^{c1}$ to $R^{c5}$ each independently represent a hydrogen atom or a substituent.

In a case where a plurality of $R^{c1}$'s exist, the plurality of $R^{c1}$'s may be the same or different from each other. The same applies to $R^{c2}$ to $R^{c5}$.

$X^1$ is the same group as $X^2$.

In Formula (1), p and q each independently represent an integer of 0 to 2.

It is preferable that p and q are each independently 0.

It is also preferable that p is the same value as q.

In Formula (1), $R^5$ and $R^6$ each independently represent a hydrogen atom or a substituent.

$R^5$ and $R^6$ are each independently preferably a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent, more preferably a hydrogen atom, an aryl group which may have a substituent, or a heteroaryl group which may have a substituent, and even more preferably a hydrogen atom.

$R^5$ and $R^6$ are not combined with each other to form a ring.

It is also preferable that $R^5$ is the same group as $R^6$.

In Formula (1), $R^1$ to $R^4$, $R^7$ to $R^{10}$, $R^{a1}$, $R^{a2}$, $R^{b1}$, and $R^{b2}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent.

$R^{a1}$, $R^{a2}$, $R^{b1}$, and $R^{b2}$ are each independently preferably a hydrogen atom, an aryl group which may have a substituent, or a heteroaryl group which may have a substituent, and more preferably a hydrogen atom.

In a case where a plurality of $R^{a1}$'s exist, the plurality of $R^{a1}$'s may be the same or different from each other. The same applies to $R^{a2}$, $R^{b1}$, and $R^{b2}$.

It is also preferable that $R^{a1}$ is the same group as $R^{b1}$.

It is also preferable that $R^{a2}$ is the same group as $R^{b2}$.

$R^1$ and $R^{10}$ are each independently preferably a hydrogen atom, an aryl group which may have a substituent, or a heteroaryl group which may have a substituent, and more preferably a hydrogen atom.

In a case where $R^1$ is a heteroaryl group which may have a substituent, an atom directly bonded to $C^1$ in $R^1$, which may have a substituent and is a heteroaryl group, is a carbon atom.

For example, in a case where $R^1$ is a carbazolyl group (carbazole group), a nitrogen atom in the carbazolyl group (carbazole group) is not directly bonded to $C^1$, and a carbon atom in the carbazolyl group (carbazole group) is directly bonded to $C^1$. In a case where the same expressions are used below, the expressions have the same meaning.

In a case where $R^{10}$ is a heteroaryl group which may have a substituent, an atom directly bonded to $C^{10}$ in $R^{10}$, which may have a substituent and is a heteroaryl group, is a carbon atom.

It is also preferable that $R^1$ is the same group as $R^{10}$.

$R^2$ and $R^9$ are each independently preferably a hydrogen atom, an aryl group which may have a substituent, or a heteroaryl group which may have a substituent, and more preferably an aryl group which may have a substituent or a heteroaryl group which may have a substituent.

Among these, $R^2$ and $R^9$ each independently preferably represent a polycyclic aryl group (for example, 2 to 6 rings) which may have a substituent, a polycyclic heteroaryl group (for example, 2 to 6 rings) which may have a substituent, or a group represented by Formula (W-1), and more preferably a polycyclic aryl group with 3 or more rings (for example, 3 to 6 rings) which may have a substituent, a polycyclic heteroaryl group (for example, 2 to 6 rings) which may have a substituent, or a group represented by Formula (W-2).

Formula (W-1) and Formula (W-2) will be described later.

It is also preferable that $R^2$ is the same group as $R^9$.

$R^3$ and $R^8$ are each independently preferably a hydrogen atom, an aryl group which may have a substituent, or a heteroaryl group which may have a substituent, and more preferably a hydrogen atom.

In a case where $R^3$ is a heteroaryl group which may have a substituent, an atom directly bonded to $C^3$ in $R^3$, which may have a substituent and is a heteroaryl group, is a carbon atom.

in a case where $R^8$ is a heteroaryl group which may have a substituent, an atom directly bonded to $C^8$ in $R^8$, which may have a substituent and is a heteroaryl group, is a carbon atom, and It is also preferable that $R^3$ is the same group as $R^8$.

$R^4$ and $R^7$ are each independently preferably a hydrogen atom, an aryl group which may have a substituent, or a heteroaryl group which may have a substituent, and more preferably a hydrogen atom.

It is also preferable that $R^4$ is the same group as $R^7$.

At least one of $R^1$ to $R^{10}$, $R^{a1}$, $R^{a2}$, $R^{b1}$, or $R^{b2}$ (more preferably at least two, even more preferably two to six, and particularly preferably two) preferably represents an aryl group which may have a substituent or a heteroaryl group which may have a substituent.

Formula (1) preferably satisfies at least one (one or both) of a requirement A or a requirement B, more preferably satisfies at least the requirement A, and even more preferably satisfies only the requirement A.

requirement A: $R^2$ and $R^9$ each independently representing an aryl group which may have a substituent or a heteroaryl group which may have a substituent, and requirement B: $R^3$ and $R^8$ each independently representing an aryl group which may have a substituent or a heteroaryl group which may have a substituent, In a case where $R^1$ to $R^{10}$, $R^{a1}$, $R^{a2}$, $R^{b1}$, and/or $R^{b2}$ (preferably $R^1$, $R^2$, $R^3$, $R^8$, $R^9$, and/or $R^{10}$, more preferably $R^2$, $R^3$, $R^8$, and/or $R^9$, and even more preferably $R^2$ and/or $R^9$) are each an aryl group which may have a substituent or a heteroaryl group which may have a substituent, the aryl group which may have a substituent or the heteroaryl group which may have a substituent is independently preferably a polycyclic aryl group (for example, 2 to 6 rings) which may have a substituent (such as a phenantrenyl group), a polycyclic heteroaryl group (for example, 2 to 6 rings) which may have a substituent, or a group represented by Formula (W-1).

The group represented by Formula (W-1) is a group shown below.

(W-1)

in Formula (W-1),*represents a bonding position,

In Formula (W-1), $Ar^1$ represents a monocyclic aromatic ring group which may have a substituent.

The monocyclic aromatic ring group may contain or may not contain one or more (preferably 1 to 3) heteroatoms (such as nitrogen atoms, sulfur atoms, oxygen atoms, selenium atoms, tellurium atoms, phosphorus atoms, silicon atoms, and/or boron atoms) as ring member atoms.

The number of ring members of the monocyclic aromatic ring group is preferably 5 to 8.

Examples of the monocyclic aromatic ring group include a benzene ring group, a furyl ring group, a pyridine ring group, a pyrazine ring group, a pyrimidine ring group, a pyridazine ring group, a triazine ring group, an oxazole ring group, a thiazole ring group, an imidazole ring group, a pyrazole ring group, an isoxazole ring group, an isothiazole ring group, an oxadiazole ring group, a thiadiazole ring group, a triazole ring group, a tetrazole ring group, a thiophene ring group, a selenophene ring group, and a pyrrole ring group.

The monocyclic aromatic ring group is preferably a benzene ring group.

Examples of a substituent which the monocyclic aromatic ring group may have include the substituent W.

The number of substituents which the monocyclic aromatic ring group may have is preferably 0 to 4, and more preferably 0.

In a case where the monocyclic aromatic ring group in $Ar^1$ has a substituent, $L^1$ and $Ar^2$ are not included as the substituents referred to herein.

In Formula (W-1), $Ar^2$ represents an aromatic ring group which may have a substituent.

The aromatic ring group may be a monocyclic aromatic ring group or a polycyclic aromatic ring group (for example, 2 to 6 rings).

The aromatic ring group may contain or may not contain one or more (preferably 1 to 3) heteroatoms (such as nitrogen atoms, sulfur atoms, oxygen atoms, selenium atoms, tellurium atoms, phosphorus atoms, silicon atoms, and/or boron atoms) as ring member atoms.

The number of ring members of the aromatic ring group is preferably 5 to 18.

Examples of the monocyclic aromatic ring group include groups similarly exemplified as the monocyclic aromatic ring group in $Ar^1$.

The polycyclic aromatic ring group is a group formed by aromatic monocycles being ring-fused with each other. In the polycyclic aromatic ring group, two or more of ring member atoms in each monocycle (aromatic monocycle) constituting a polycyclic aromatic ring are ring member atoms in another monocycle (aromatic monocycle) constituting the polycyclic aromatic ring group.

Examples of the polycyclic aromatic ring group include a naphthalene ring group, an anthracene ring group, a phenanthrene ring group, a quinoline ring group, an isoquinoline ring group, an acridine ring group, a phenanthridine ring group, a pteridine ring group, a quinoxaline ring group, a quinazoline ring group, a cinnoline ring group, a phthalazine ring group, a benzoxazole ring group, a benzothiazole ring group, a benzimidazole ring group, an indazole ring group, a benzoisoxazole ring group, a benzisothiazol ring group, a benzofuran ring group, a benzothiophene ring group, a benzoselenophene ring group, a dibenzofuran ring group, a dibenzothiophene ring group, a dibenzoselenophene ring group, a thienothiophene ring group, a thienopyrrole ring group, a dithienopyrrole ring group, an indole ring group, an imidazopyridine ring group, and a carbazole ring group.

The aromatic ring group is preferably a benzene ring group or a polycyclic aromatic heterocyclic group, and more preferably a benzene ring group or a benzothiophene ring group.

Examples of a substituent which the aromatic ring group may have include the examples exemplified as the substituent W, and among these, a halogen atom (such as a chlorine atom), an alkyl group (such as a methyl group) which may have a substituent, and the like, an alkoxy group (such as a methoxy group) which may have a substituent, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent is preferable, and a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent is more preferable.

The number of substituents which the aromatic ring group may have is preferably 0 to 9, and more preferably 0 and 1.

In a case where the aromatic ring group in $Ar^2$ has a substituent, $L^1$ is not included as the substituent referred to herein.

In Formula (W-1), r represents 0 or 1.

r is preferably 0.

In Formula (W-1), $L^1$ represents a sulfur atom (—S—), an oxygen atom (—O—), a selenium atom (—Se—), $SiR^{w1}R^{w2}$ (—$SiR^{w1}R^{w2}$—), $NR^{w3}$ (—$NR^{w3}$—), or $CR^{w4}R^{w5}$ (—$CR^{w4}R^{w5}$—).

$R^{w1}$ to $R^{w5}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent.

Here, in a case where r represents 0, $L^1$ does not exist, and $Ar^1$ and $Ar^2$ are connected only by a single bond specified in Formula (W-1).

In a case where $R^1$ to $R^{10}$, $R^{a1}$, $R^{a2}$, $R^{b1}$, and/or $R^{b2}$ (preferably $R^1$, $R^2$, $R^3$, $R^8$, $R^9$, and/or $R^{10}$, more preferably $R^2$, $R^3$, $R^8$, and/or $R^9$, and even more preferably $R^2$ and/or $R^9$) are each an aryl group which may have a substituent or a heteroaryl group which may have a substituent, the aryl group which may have a substituent or the heteroaryl group which may have a substituent is independently more preferably a polycyclic aryl group (such as a phenantrenyl group) with 3 or more rings (for example, 3 to 6 rings) which may have a substituent, a polycyclic heteroaryl group (for example, 2 to 6 rings) which may have a substituent, or a group represented by Formula (W-2).

The group represented by Formula (W-2) is a group illustrated below.

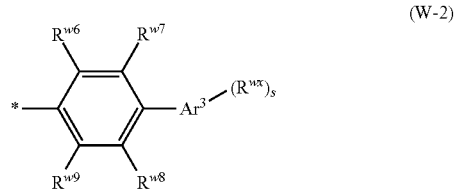

In Formula (W-2),*represents a bonding position.

In Formula (W-2), $R^{w6}$ to $R^{w9}$ each independently represent a hydrogen atom, a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent.

An alkoxy group and an alkylthio group which the aryl group and the heteroaryl group may have, as a substituent, each may further have a substituent.

In Formula (W-2), $Ar^3$ represents a benzene ring group or a polycyclic aromatic heterocyclic group.

The polycyclic aromatic heterocyclic group in $Ar^3$ is, for example, the same as the aromatic heterocyclic group containing a hetero atom in the polycyclic aromatic ring group described with respect to Formula (W-1).

Specific examples of the polycyclic aromatic heterocyclic group in $Ar^3$ include groups similarly included in the aromatic heterocyclic group, among the groups exemplified as specific examples of the polycyclic aromatic ring group described with respect to Formula (W-1).

The polycyclic aromatic heterocyclic group in $Ar^3$ is preferably a benzothiophene ring group.

In Formula (W-2), $R^{wx}$ represents a halogen atom, an alkylthio group which may have a substituent, an aryl group which may have a group selected from the group consisting of a halogen atom, an alkoxy group, and an alkylthio group as a substituent, or a heteroaryl group which may have a group selected from the group consisting of a halogen atom, an alkoxy group, and an alkylthio group as a substituent.

An alkoxy group and an alkylthio group which the aryl group and the heteroaryl group may have, as a substituent, each may further have a substituent.

In a case where a plurality of $R^{wx}$'s exist, the plurality of $R^{wx}$'s may be the same or different from each other.

In Formula (W-2), s represents an integer of 0 or more.

The value of s means the number of hydrogen atoms substituted by a group represented by $R^{wx}$ among hydrogen atoms which a benzene ring group or a polycyclic aromatic heterocyclic group represented by $Ar^3$ may have.

In a case where s is 0, the benzene ring group or the polycyclic aromatic heterocyclic group represented by $Ar^3$ is unsubstituted. In a case where the benzene ring group or the polycyclic aromatic heterocyclic group is unsubstituted, it is permissible for the unsubstituted benzene ring group or the polycyclic aromatic heterocyclic group to have a hydrogen atom.

Here, in a case where $Ar^3$ is a benzene ring group, s represents an integer of 0 to 5.

In a case where $Ar^3$ is a polycyclic aromatic heterocyclic group, the value of s is not limited as long as the value of s is equal to or less than the number of substituents which the polycyclic aromatic heterocyclic group represented by $Ar^3$ may have. For example, in a case where $Ar^3$ is a polycyclic aromatic heterocyclic group, s is an integer of 0 to 5.

In a case where $Ar^3$ is a benzene ring group and s is 1 or more, at least one of substituents ($R^{wx}$) of the benzene ring group represented by $Ar^3$ is also preferably present at a para position with respect to a bonding position with the benzene ring group specified in Formula (W-2).

(Compound Represented by Formula (2))

From the viewpoint that the effect of the present invention is more excellent, the compound represented by Formula (1) is preferably a compound represented by Formula (2).

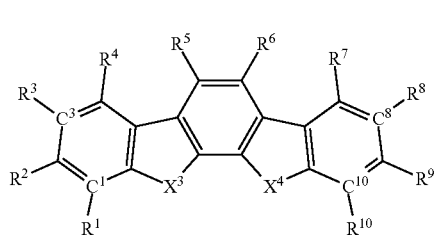

(2)

in Formula (2), $C^1$, $C^3$, $C^8$, and $C^{10}$ each represent a carbon atom,

In Formula (2), $X^3$ and $X^4$ each independently represent a sulfur atom or an oxygen atom.

$X^3$ and $X^4$ each independently preferably represent a sulfur atom.

In Formula (2), $R^5$ and $R^6$ each independently represent a hydrogen atom or a substituent.

$R^5$ and $R^6$ in Formula (2) are the same as $R^5$ and $R^6$ in Formula (1), respectively.

In Formula (2), $R^1$ to $R^4$ and $R^7$ to $R^{10}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent.

Here, in a case where $R^1$ is a heteroaryl group which may have a substituent, an atom directly bonded to $C^1$ in $R^1$, which may have a substituent and is a heteroaryl group, is a carbon atom.

In a case where $R^3$ is a heteroaryl group which may have a substituent, an atom directly bonded to $C^3$ in $R^3$, which may have a substituent and is a heteroaryl group, is a carbon atom.

In a case where $R^8$ is a heteroaryl group which may have a substituent, an atom directly bonded to $C^8$ in $R^8$, which may have a substituent and is a heteroaryl group, is a carbon atom.

In a case where $R^{10}$ is a heteroaryl group which may have a substituent, an atom directly bonded to $C^{10}$ in $R^{10}$, which may have a substituent and is a heteroaryl group, is a carbon atom.

$R^1$ to $R^4$ and $R^7$ to $R^{10}$ in Formula (2) are the same as $R^1$ to $R^4$ and $R^7$ to $R^{10}$ in Formula (1), respectively.

In Formula (2), at least one (one or both) of a requirement A or a requirement B is satisfied. It is more preferable that Formula (2) satisfies at least the requirement A, and it is even more preferable that Formula (2) satisfies only requirement A.

Requirement A: $R^2$ and $R^9$ each independently representing an aryl group which may have a substituent or a heteroaryl group which may have a substituent Requirement B: $R^3$ and $R^8$ each independently representing an aryl group which may have a substituent or a heteroaryl group which may have a substituent The requirement A and the requirement B in Formula (2) are the same as the requirement A and the requirement B described with respect to Formula (1), respectively.

(Compound Represented by Formula (3))

The compound represented by Formula (1) is also preferably a compound represented by Formula (3).

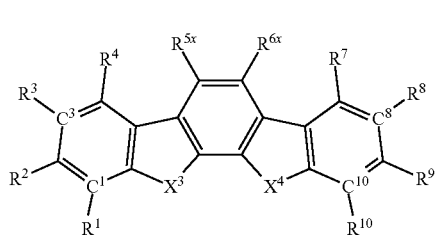

(3)

In Formula (3), $C^1$, $C^3$, $C^8$, and $C^{10}$ each represent a carbon atom.

In Formula (3), $X^3$ and $X^4$ each independently represent a sulfur atom or an oxygen atom.

$X^3$ and $X^4$ each independently preferably represent a sulfur atom.

In Formula (3), $R^1$ to $R^4$, $R^7$ to $R^{10}$, $R^{5x}$, and $R^{6x}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent.

Here, in a case where $R^1$ is a heteroaryl group which may have a substituent, an atom directly bonded to $C^1$ in $R^1$, which may have a substituent and is a heteroaryl group, is a carbon atom.

In a case where $R^3$ is a heteroaryl group which may have a substituent, an atom directly bonded to $C^3$ in $R^3$, which may have a substituent and is a heteroaryl group, is a carbon atom.

In a case where $R^8$ is a heteroaryl group which may have a substituent, an atom directly bonded to $C^8$ in $R^8$, which may have a substituent and is a heteroaryl group, is a carbon atom.

In a case where $R^{10}$ is a heteroaryl group which may have a substituent, an atom directly bonded to $C^{10}$ in $R^{10}$, which may have a substituent and is a heteroaryl group, is a carbon atom, $R^1$ to $R^4$ and $R^7$ to $R^{10}$ in Formula (3) are the same as $R^1$ to $R^4$ and $R^7$ to $R^{10}$ in Formula (1), respectively.

$R^{5x}$ and $R^{6x}$ in Formula (3) each have the form in which $R^5$ and $R^6$ in Formula (1) are each limited to a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent.

In Formula (3), at least one (one or both) of the requirement A and the requirement B is satisfied. It is more preferable that Formula (3) satisfies at least the requirement A, and it is even more preferable that Formula (3) satisfies only requirement A.

Requirement A: $R^2$ and $R^9$ each independently representing an aryl group which may have a substituent or a heteroaryl group which may have a substituent Requirement B: $R^3$ and $R^8$ each independently representing an aryl group which may have a substituent or a heteroaryl group which may have a substituent The requirement A and the requirement B in Formula (3) are the same as the requirement A and the requirement B described with respect to Formula (1), respectively.

(Compound Represented by Formula (4))

The compound represented by Formula (1) is also preferably a compound represented by Formula (4).

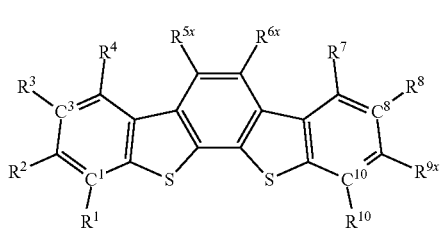

(4)

In Formula (4), $R^1$, $R^3$, $R^4$, $R^7$, $R^8$, $R^{10}$, $R^{5x}$, and $R^{6X}$ each independently represent a hydrogen atom, a halogen atom, an alkyl group which may have a substituent, an alkoxy group which may have a substituent, an alkylthio group which may have a substituent, a silyl group which may have a substituent, an alkenyl group which may have a substituent, an alkynyl group which may have a substituent, an aryl group which may have a substituent, or a heteroaryl group which may have a substituent.

In a case where $R^3$ is a heteroaryl group which may have a substituent, an atom directly bonded to $C^3$ in $R^3$, which may have a substituent and is a heteroaryl group, is a carbon atom.

In a case where $R^8$ is a heteroaryl group which may have a substituent, an atom directly bonded to $C^8$ in $R^8$, which may have a substituent and is a heteroaryl group, is a carbon atom.

In a case where $R^{10}$ is a heteroaryl group which may have a substituent, an atom directly bonded to $C^{10}$ in $R^{10}$, which may have a substituent and is a heteroaryl group, is a carbon atom, $R^1$, $R^3$, $R^4$, $R^7$, $R^8$, $R^{10}$, $R^{5x}$, and $R^{6x}$ in Formula (4) are the same as $R^1$, $R^3$, $R^4$, $R^7$, $R^8$, $R^{10}$, $R^{5x}$, and $R^{6x}$ in Formula (3), respectively.

In Formula (4), $R^{2x}$ and $R^{9x}$ each independently represent a polycyclic aryl group with 3 or more rings (for example, 3 to 6 rings) which may have a substituent, a polycyclic heteroaryl group (for example, 2 to 6 rings) which may have a substituent, or a group represented by Formula (W-2).

A group that may be formed by $R^{2x}$ and $R^{9x}$ and that is represented by Formula (W-2) in Formula (4) is the same as the group represented by Formula (W-2) described with respect to Formula (1).

A molecular weight of the specific compound is not particularly limited, but is preferably 260 to 1200, and more preferably 400 to 900. In a case where the molecular weight is 1200 or less, a vapor deposition temperature is not increased, and the compound is not easily decomposed. In a case where the molecular weight of the compound is 260 or more, a glass transition point of a vapor deposition film is not lowered, and the heat resistance of the photoelectric conversion element is improved.

The specific compound may be used alone, or two or more thereof may be used in combination.

The specific structure of the specific compounds are exemplified below.

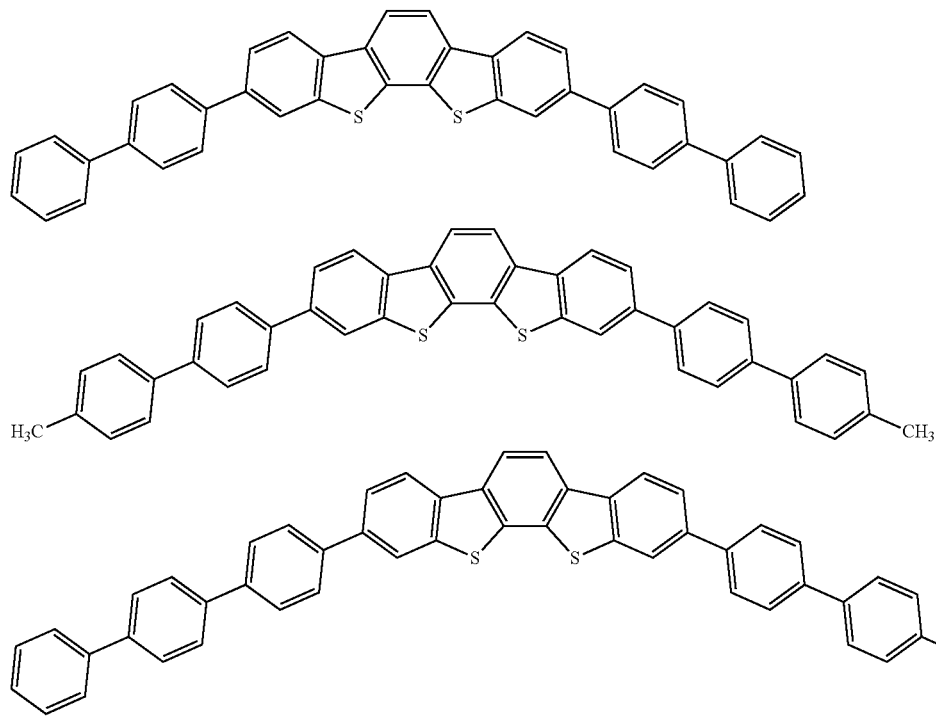

-continued
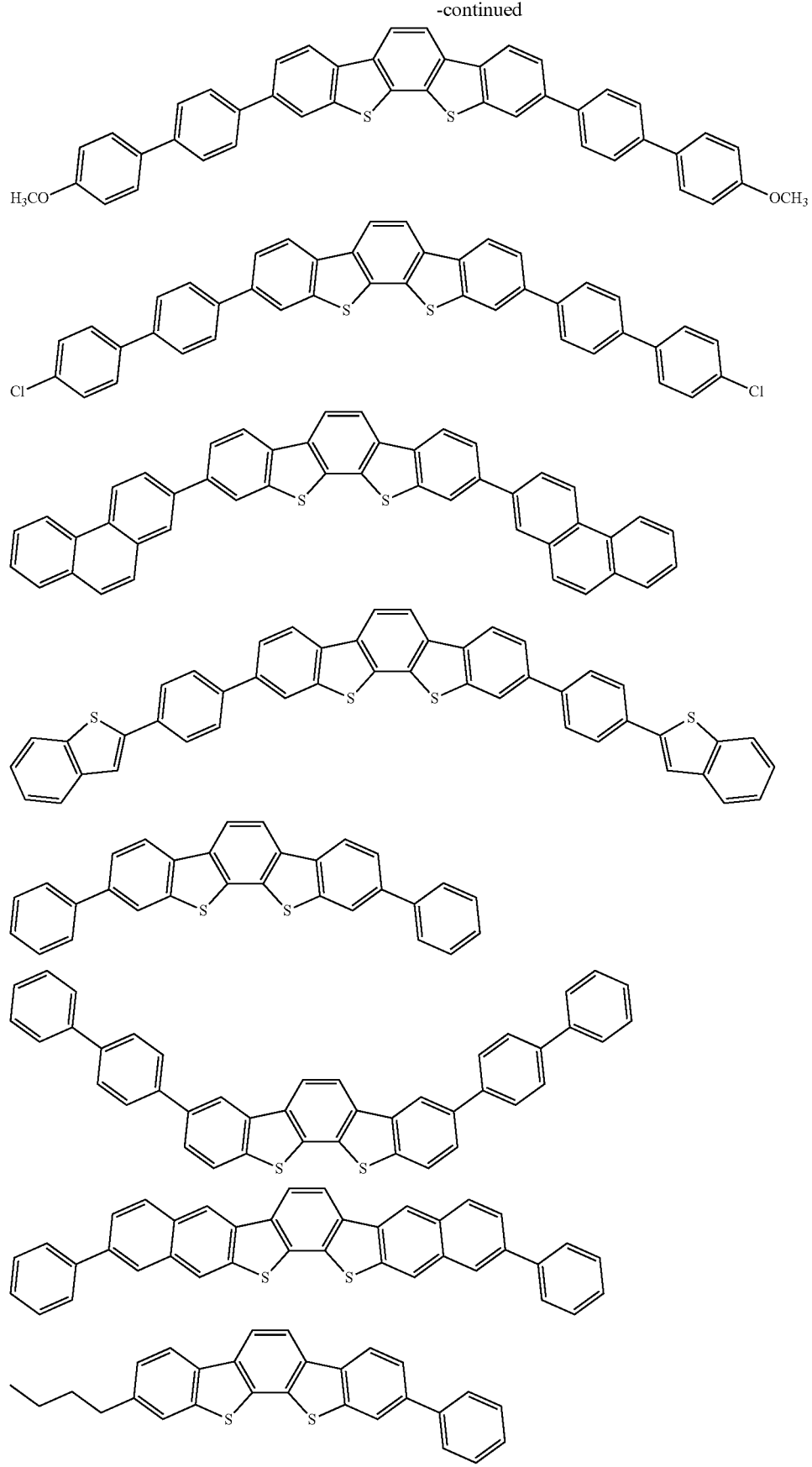

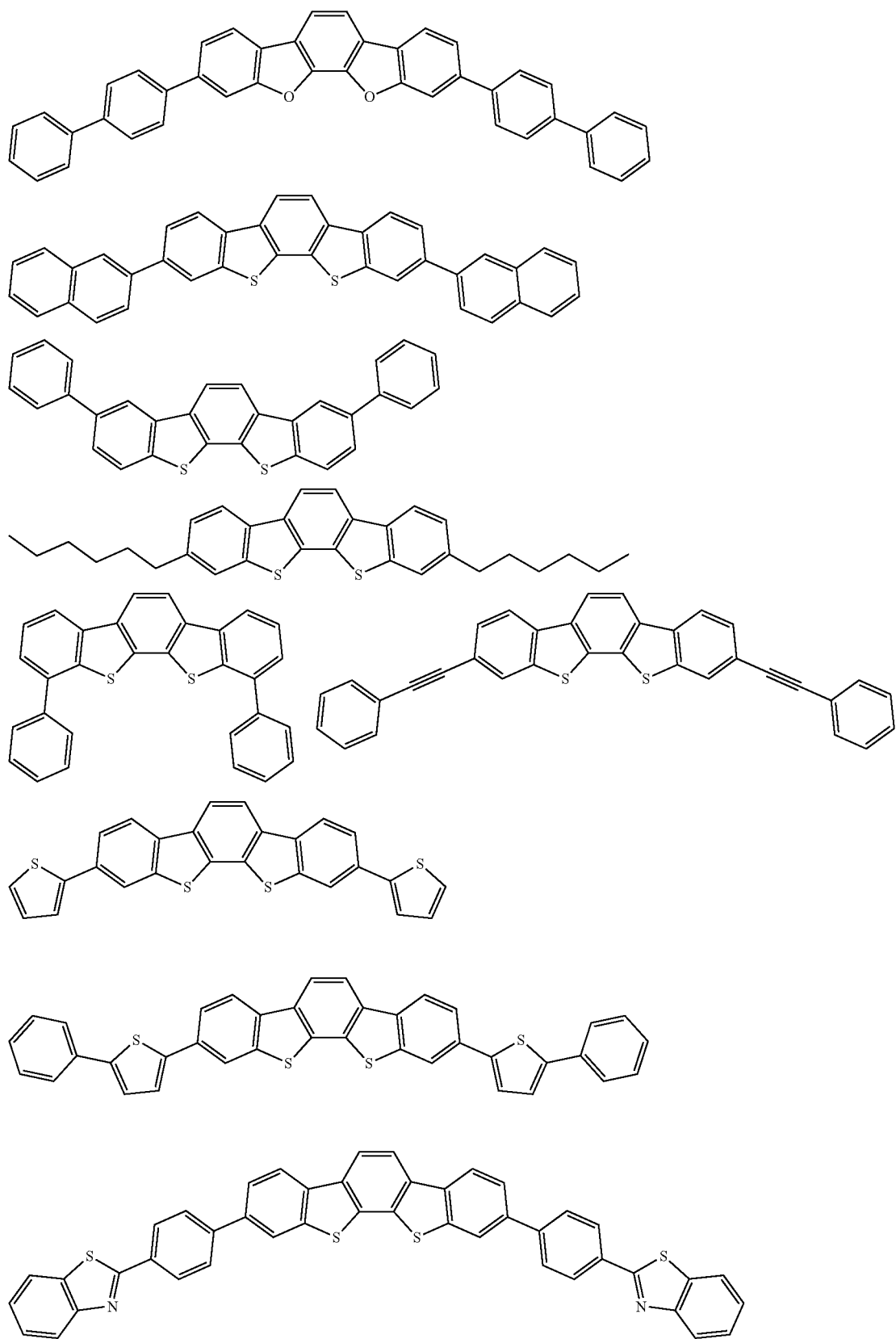

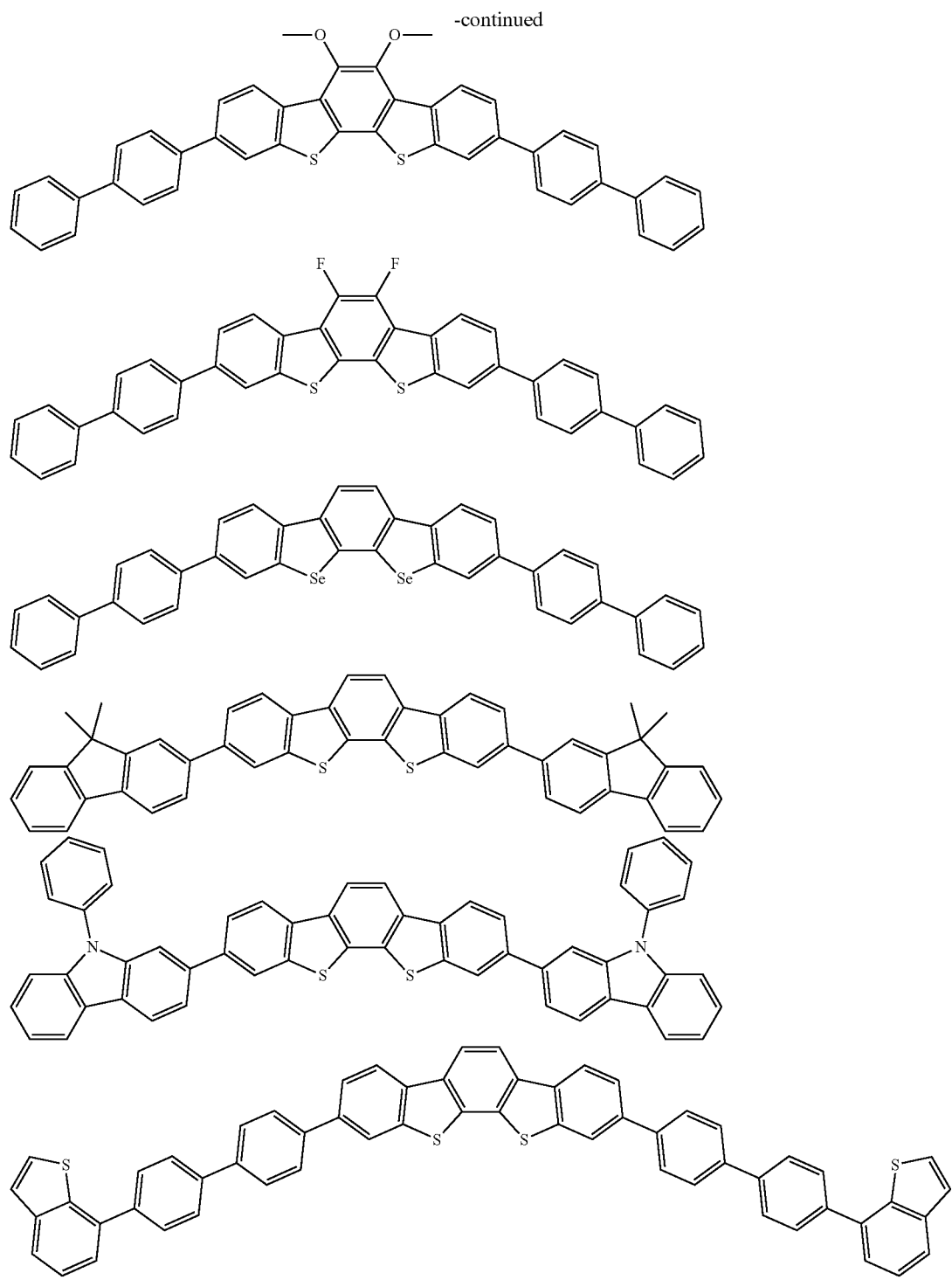

The specific compound is particularly useful as a material of the photoelectric conversion film used for the imaging element, the optical sensor, or a photoelectric cell. The specific compound can also be used as a coloring material, a liquid crystal material, an organic semiconductor material, a charge transport material, a pharmaceutical material, and a fluorescent diagnostic material.

The specific compound is preferably a compound in which an ionization potential in a single film is −5.0 to −6.0 eV from the viewpoints of matching of energy levels between the compound and the n-type semiconductor material described later.

A maximum absorption wavelength of the specific compound is not particularly limited, and for example, is preferably within a range of 300 to 500 nm.

The maximum absorption wavelength is a value measured in a solution state (solvent: chloroform) by an absorption spectrum of the specific compound being adjusted to a concentration having an absorbance of about 0.5 to 1.

A maximum absorption wavelength of the photoelectric conversion film is not particularly limited, and for example, is preferably within a range of 300 to 700 nm.

<N-Type Semiconductor Material>

The photoelectric conversion film contains the n-type semiconductor material as another component in addition to the specific compound. The n-type semiconductor material is an acceptor-property organic semiconductor material (a compound), and refers to an organic compound having a property of easily accepting an electron.

More specifically, the n-type semiconductor material refers to an organic compound having a higher electron affinity than that of the specific compound in a case where the n-type semiconductor material is used by being brought in contact with the above-described specific compound.

In the present specification, a value (value multiplied by −1) of a reciprocal number of the LUMO value obtained by the calculation of B3LYP/6-31G (d) using Gaussian '09 (software manufactured by Gaussian, Inc.) as a value of the electron affinity.

The electron affinity of the n-type semiconductor material is preferably 3.0 to 5.0 eV.

Examples of the n-type semiconductor material include fullerenes selected from the group consisting of a fullerene and derivatives thereof, fused aromatic carbocyclic compounds (for example, a naphthalene derivative, an anthracene derivative, a phenanthrene derivative, a tetracene derivative, a pyrene derivative, a perylene derivative, and a fluoranthene derivative); a heterocyclic compound having a 5- to 7-membered ring having at least one of a nitrogen atom, an oxygen atom, or a sulfur atom (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, and thiazole); polyarylene compounds; fluorene compounds; cyclopentadiene compounds; silyl compounds; 1,4,5,8-naphthalenetetracarboxylic acid anhydride; 1,4,5,8-naphthalenetetracarboxylic acid anhydride imide derivative; oxadiazole derivative; anthraquinodimethane derivatives; diphenylquinone derivatives; bathocuproine, bathophenanthroline, and derivatives thereof; triazole compounds; a distyrylarylene derivative; a metal complex having a nitrogen-containing heterocyclic compound as a ligand; a silole compound; and compounds disclosed in paragraphs [0056] to [0057] of JP2006-100767A.

Among these, it is preferable that examples of the n-type semiconductor material include fullerenes selected from the group consisting of a fullerene and derivatives thereof.

Examples of the fullerenes include a fullerene C60, a fullerene C70, a fullerene C76, a fullerene C78, a fullerene C80, a fullerene C82, a fullerene C84, a fullerene C90, a fullerene C96, a fullerene C240, a fullerene C540, and a mixed fullerene.

Examples of the fullerene derivatives include compounds in which a substituent is added to the above fullerenes. The substituent is preferably an alkyl group, an aryl group, or a heterocyclic group. The fullerene derivative is preferably compounds described in JP2007-123707A.

In a case where the n-type semiconductor material includes fullerenes, a content of the fullerenes to a total content of the n-type semiconductor material in the photoelectric conversion film (=(film thickness of fullerenes in terms of single layer/film thickness of total n-type semiconductor material in terms of single layer)×100) is preferably 15% to 100% by volume, more preferably 35% to 100% by volume.

An organic coloring agent may be used as the n-type semiconductor material in place of the n-type semiconductor material described in the upper row or together with the n-type semiconductor material described in the upper row.

By using an organic coloring agent as the n-type semiconductor material, it is easy to control an absorption wavelength (maximum absorption wavelength) of the photoelectric conversion element to be within any wavelength range.

Examples of the organic coloring agent include a cyanine coloring agent, a styryl coloring agent, a hemicyanine coloring agent, a merocyanine coloring agent (including zeromethine merocyanine (simple merocyanine)), a rhodacyanine coloring agent, an allopolar coloring agent, an oxonol coloring agent, a hemioxonol coloring agent, a squarylium coloring agent, a croconium coloring agent, an azamethine coloring agent, a coumarin coloring agent, an arylidene coloring agent, an anthraquinone coloring agent, a triphenylmethane coloring agent, an azo coloring agent, an azomethine coloring agent, a metallocene coloring agent, a fluorenone coloring agent, a flugide coloring agent, a perylene coloring agent, a phenazine coloring agent, a phenothiazine coloring agent, a quinone coloring agent, a diphenylmethane coloring agent, a polyene coloring agent, an acridine coloring agent, an acridinone coloring agent, a diphenylamine coloring agent, a quinophthalone coloring agent, a phenoxazine coloring agent, a phthaloperylene coloring agent, a dioxane coloring agent, a porphyrin coloring agent, a chlorophyll coloring agent, a phthalocyanine coloring agent, a subphthalocyanine coloring agent, a metal complex coloring agent, compounds disclosed in paragraphs [0083] to [0089] of JP2014-82483A, compounds disclosed in paragraphs [0029] to [0033] of JP2009-167348A, compounds disclosed in paragraphs [0197] to [0227] of JP2012-77064A, compounds disclosed in paragraphs [0035] to [0038] of WO2018-105269A, compounds disclosed in paragraphs [0041] to [0043] of WO2018-186389A, compounds disclosed in paragraphs [0059] to [0062] of WO2018-186397A, compounds disclosed in paragraphs [0078] to [0083] of WO2019-009249A, compounds disclosed in paragraphs [0054] to [0056] of WO2019-049946A, compounds disclosed in paragraphs [0059] to [0063] of WO2019-054327A, and compounds disclosed in paragraphs [0086] to [0087] of WO2019-098161A.

In a case where the n-type semiconductor material includes an organic coloring agent, a content of the organic coloring agent to a total content of the n-type semiconductor material in the photoelectric conversion film (=(film thickness of organic coloring agent in terms of single layer/film thickness of total n-type semiconductor material in terms of single layer)×100) is preferably 15% to 100% by volume, more preferably 35% to 100% by volume.

The molecular weight of the n-type semiconductor material is preferably 200 to 1200, and more preferably 200 to 1000.

It is preferable that the photoelectric conversion film has a bulk hetero structure formed in a state where the specific compound and the n-type semiconductor material are mixed. The bulk hetero structure refers to a layer in which the specific compound and the n-type semiconductor material are mixed and dispersed in the photoelectric conversion film. The bulk hetero structure is described in detail in, for example, paragraphs [0013] and [0014] of JP2005-303266A and the like.

From the viewpoint of responsiveness of the photoelectric conversion element, a content of the specific compound to a total content of the specific compound and the n-type semiconductor material (=film thickness of specific compound in terms of a single layer/(film thickness of specific compound in terms of single layer+film thickness of n-type semiconductor material in terms of single layer)×100) is preferably 15% to 75% by volume, and more preferably 35% to 75% by volume.

The photoelectric conversion film is substantially preferably constituted of the specific compound and the n-type semiconductor material. The term "substantially" means that the total content of the specific compound and the n-type semiconductor material is 95% by mass or more with respect to a total mass of the photoelectric conversion film.

The n-type semiconductor material contained in the photoelectric conversion film may be used alone, or two or more thereof may be used in combination.

The photoelectric conversion film containing the specific compound is a non-light emitting film, and has a feature different from an organic light emitting diode (OLED). The non-light emitting film means a film having a light emission quantum efficiency of 1% or less, and the light emission quantum efficiency is preferably 0.5% or less, and more preferably 0.1% or less.

<Film Formation Method>

The photoelectric conversion film can be formed mostly by a dry film formation method. Examples of the dry film formation method include a physical vapor deposition method such as a vapor deposition method (in particular, a vacuum evaporation method), a sputtering method, and an ion plating method, a molecular beam epitaxy (MBE) method, and a chemical vapor deposition (CVD) method such as plasma polymerization. Among these, the vacuum evaporation method is preferable. In a case where the photoelectric conversion film is formed by the vacuum evaporation method, manufacturing conditions such as a degree of vacuum and a vapor deposition temperature can be set according to the normal method.

The thickness of the photoelectric conversion film is preferably 10 to 1000 nm, more preferably 50 to 800 mm, even more preferably 50 to 500 nm, and particularly preferably 50 to 300 nm.

<Electrode>

Electrodes (the upper electrode (the transparent conductive film) 15 and the lower electrode (the conductive film) 11) are formed of conductive materials. Examples of the conductive material include metals, alloys, metal oxides, electrically conductive compounds, and mixtures thereof.

Since light is incident through the upper electrode 15, the upper electrode 15 is preferably transparent to light to be detected. Examples of the materials constituting the upper electrode 15 include conductive metal oxides such as tin oxide (antimony tin oxide (ATO), fluorine doped tin oxide (FTO)) doped with antimony, fluorine, or the like, tin oxide, zinc oxide, indium oxide, indium tin oxide (ITO), and indium zinc oxide (IZO); metal thin films such as gold, silver, chromium, and nickel; mixtures or laminates of these metals and the conductive metal oxides; and organic conductive materials such as polyaniline, polythiophene, and polypyrrole. Among these, conductive metal oxides are preferable from the viewpoints of high conductivity, transparency, and the like.

In general, in a case where the conductive film is made to be thinner than a certain range, a resistance value is rapidly increased. However, in the solid-state imaging element into which the photoelectric conversion element according to the present embodiment is incorporated, the sheet resistance is preferably 100 to 10000Ω/□, and a degree of freedom of a range of the film thickness that can be thinned is large. In addition, as the thickness of the upper electrode (the transparent conductive film) 15 is thinner, the amount of light that the upper electrode absorbs is smaller, and the light transmittance usually increases. The increase in the light transmittance causes an increase in light absorbance in the photoelectric conversion film and an increase in the photoelectric conversion ability, which is preferable. Considering the suppression of leakage current, an increase in the resistance value of the thin film, and an increase in transmittance accompanied by the thinning, the film thickness of the upper electrode 15 is preferably 5 to 100 nm, and more preferably 5 to 20 nm.

There is a case where the lower electrode 11 has transparency or an opposite case where the lower electrode does not have transparency and reflects light, depending on the application. Examples of a material constituting the lower electrode 11 include conductive metal oxides such as tin oxide (ATO, FTO) doped with antimony, fluorine, or the like, tin oxide, zinc oxide, indium oxide, indium tin oxide (ITO), and indium zinc oxide (IZO); metals such as gold, silver, chromium, nickel, titanium, tungsten, and aluminum, conductive compounds (for example, titanium nitride (TiN)) such as oxides or nitrides of these metals; mixtures or laminates of these metals and conductive metal oxides; and organic conductive materials such as polyaniline, polythiophene, and polypyrrole.

The method of forming electrodes is not particularly limited, and can be appropriately selected in accordance with the electrode material. Specific examples thereof include a wet method such as a printing method and a coating method; a physical method such as a vacuum evaporation method, a sputtering method, and an ion plating method; and a chemical method such as a CVD method and a plasma CVD method.

In a case where the material of the electrode is ITO, examples thereof include an electron beam method, a sputtering method, a resistance heating vapor deposition method, a chemical reaction method (such as a sol-gel method), and a coating method with a dispersion of indium tin oxide.

<Charge Blocking Film: Electron Blocking Film and Positive Hole Blocking Film>

It is also preferable that the photoelectric conversion element according to the embodiment of the present invention has one or more interlayers between the conductive film and the transparent conductive film, in addition to the photoelectric conversion film. An example of the interlayer includes a charge blocking film. In a case where the photoelectric conversion element has this film, the characteristics (such as photoelectric conversion efficiency and responsiveness) of the obtained photoelectric conversion element are more excellent. Examples of the charge blocking film include an electron blocking film and a positive hole blocking film. Hereinafter, each of the films will be described in detail.

(Electron Blocking Film)

The electron blocking film is a donor organic semiconductor material (compound), and a p-type organic semiconductor described below can be used, for example. The p-type organic semiconductor may be used alone, or two or more thereof may be used in combination.

Examples of the p-type organic semiconductor include triarylamine compounds (for example, N, N'-bis (3-methylphenyl)-(1,1'-biphenyl)-4,4'-diamine (TPD), 4,4'-bis [N-(naphthyl)-N-Phenyl-amino] biphenyl (α-NPD), compounds disclosed in paragraphs [0128] to [0148] of JP2011-228614A, compounds disclosed in paragraphs [0052] to [0063] of JP2011-176259A, compounds disclosed in paragraphs [0119] to [0158] of JP2011-225544A, compounds disclosed in paragraphs [0044] to [0051] of JP2015-153910A, and compounds disclosed in paragraphs [0086] to [0090] of JP2012-94660A, pyrazoline compounds, styrylamine compounds, hydrazone compounds, polysilane compounds, thiophene compounds (for example, a thienothiophene derivative, a dibenzothiophene derivative, a benzodithiophene derivative, a dithienothiophene derivative, a [1] benzothieno [3,2-b] thiophene (BTBT) derivative, a thieno [3,2-f: 4,5-f] bis [1] benzothiophene (TBBT) derivative, compounds disclosed in paragraphs [0031] to [0036] of JP2018-14474A, compounds disclosed in paragraphs [0043] to [0045] of WO2016-194630A, compounds disclosed in paragraphs [0025] to [0037], and [0099] to [0109] of WO2017-159684A, compounds disclosed in paragraphs [0029] to [0034] of JP2017-076766A, compounds disclosed in paragraphs [0015] to [0025] of WO2018-207722A, compounds disclosed in paragraphs [0045] to [0053] of JP2019-54228A, compounds disclosed in paragraphs [0045] to [0055] of WO2019-058995A, compounds disclosed in paragraphs [0063] to [0089] of WO2019-081416A, compounds disclosed in paragraphs [0033] to [0036] of JP2019-80052A, compounds disclosed in paragraphs [0044] to [0054] of WO2019-054125A, compounds disclosed in paragraphs [0041] to [0046] of WO2019-093188A, and the like), a cyanine compound, an oxonol compound, a polyamine compound, an indole compound, a pyrrole compound, a pyrazole compound, a polyarylene compound, a fused aromatic carbocyclic compound (for example, a naphthalene derivative, an anthracene derivative, a phenanthrene derivative, a tetracene derivative, a pentacene derivative, a pyrene derivative, a perylene derivative, and a fluoranthene derivative), a porphyrin compound, a phthalocyanine compound, a triazole compound, an oxadiazole compound, an imidazole compound, a polyarylalkane compound, a pyrazolone compound, an amino-substituted chalcone compound, an oxazole compound, a fluorenone compound, a silazane compound, and a metal complex having nitrogen-containing heterocyclic compounds as ligands.

Examples of the p-type organic semiconductor include compounds having an ionization potential smaller than that of the n-type semiconductor material, and in a case where this condition is satisfied, the organic coloring agents exemplified as the n-type semiconductor material can be used.

A polymer material can also be used as the electron blocking film.

Examples of the polymer material include a polymer such as phenylenevinylene, fluorene, carbazole, indole, pyrene, pyrrole, picoline, thiophene, acetylene, and diacetylene, and a derivative thereof.

The electron blocking film may be formed of a plurality of films.

The electron blocking film may be formed of an inorganic material. In general, since an inorganic material has a dielectric constant larger than that of an organic material, in a case where the inorganic material is used in the electron blocking film, a large voltage is applied to the photoelectric conversion film. Therefore, the photoelectric conversion efficiency increases. Examples of the inorganic material that can be used for the electron blocking film include calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide.

(Positive Hole Blocking Film)

A positive hole blocking film is an acceptor-property organic semiconductor material (compound), and the n-type semiconductor material described above can be used.

The method of manufacturing the charge blocking film is not particularly limited, and examples thereof include a dry film formation method and a wet film formation method. Examples of the dry film formation method include a vapor deposition method and a sputtering method. The vapor deposition method may be any of a physical vapor deposition (PVD) method and a chemical vapor deposition (CVD) method, and the physical vapor deposition method such as a vacuum evaporation method is preferable. Examples of the wet film formation method include an ink jet method, a spray method, a nozzle printing method, a spin coating method, a dip coating method, a casting method, a die coating method, a roll coating method, a bar coating method, and a gravure coating method, and an ink jet method is preferable from the viewpoint of high accuracy patterning.

Each thickness of the charge blocking films (the electron blocking film and the positive hole blocking film) is preferably 3 to 200 nm, more preferably 5 to 100 nm, and even more preferably 5 to 30 nm.

<Substrate>

The photoelectric conversion element may further include a substrate. Types of the substrate to be used are not particularly limited, and examples of the substrate include a semiconductor substrate, a glass substrate, and a plastic substrate.

A position of the substrate is not particularly limited, and in general, the conductive film, the photoelectric conversion film, and the transparent conductive film are laminated on the substrate in this order.

<Sealing Layer>

The photoelectric conversion element may further include a sealing layer. The performance of a photoelectric conversion material may deteriorate noticeably due to the presence of deterioration factors such as water molecules. The deterioration can be prevented by coating and sealing the entirety of the photoelectric conversion film with the sealing layer such as diamond-like carbon (DLC) or ceramics such as metal oxide, or metal nitride, and metal nitride oxide which are dense and into which water molecules do not permeate.

The material of the sealing layer may be selected and the sealing layer may be manufactured according to the description in paragraphs [0210] to [0215] of JP2011-082508A.

<Imaging Element>

An example of the application of the photoelectric conversion element includes an imaging element. The imaging element is an element that converts optical information of an image into an electric signal. In general, a plurality of the photoelectric conversion elements are arranged in a matrix on the same plane, and an optical signal is converted into an electric signal in each photoelectric conversion element (pixel) to sequentially output the electric signal to the outside of the imaging element for each pixel. Therefore, each pixel is formed of one or more photoelectric conversion elements and one or more transistors.

Figure 3:
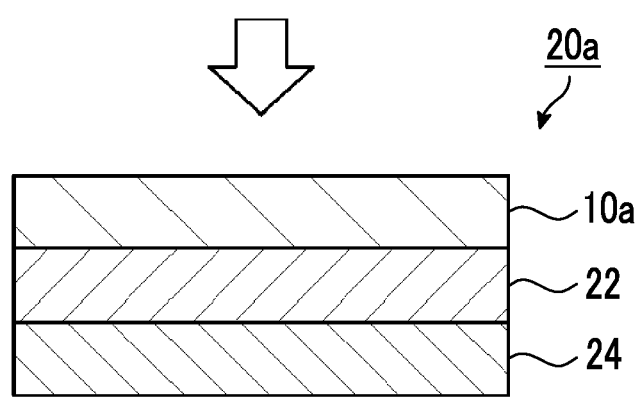
FIG. 3 is a schematic cross-sectional view of an embodiment of an imaging element.

FIG. 3 is a schematic cross-sectional view illustrating a schematic configuration of an imaging element for describing an embodiment of the present invention. This imaging element is mounted on an imaging element such as a digital camera and a digital video camera, an electronic endoscope, and imaging modules such as a cellular phone.

An imaging element 20a illustrated in FIG. 3 includes a photoelectric conversion element 10a (a green photoelectric conversion element 10a) according to the embodiment of the present invention, a blue photoelectric conversion element 22, and a red photoelectric conversion element 24, which are laminated along a light incident direction. The photoelectric conversion element 10a is a photoelectric conversion element according to the embodiment of the present invention, and is mostly used as a green photoelectric conversion element by the control of an absorption wavelength so that green light can be received. An example of a method of controlling the absorption wavelength of the photoelectric conversion element according to the embodiment of the present invention includes a method of using an organic coloring agent suitable as the n-type semiconductor material.

The imaging element 20a is a so-called laminated-type color separation imaging element. The photoelectric conversion element 10a, the blue photoelectric conversion element 22, and the red photoelectric conversion element 24 have different wavelength spectra to be detected. That is, the blue photoelectric conversion element 22 and the red photoelectric conversion element 24 correspond to photoelectric conversion elements that receive (absorb) light having a wavelength different from a wavelength of light received by the photoelectric conversion element 10a. The photoelectric conversion element 10a can mostly receive green light, the blue photoelectric conversion element 22 can mostly receive blue light, and the red photoelectric conversion element can mostly receive red light.

Green light means light in a wavelength range of 500 to 600 nm, blue light means light in a wavelength range of 400 to 500 nm, and red light means light in a wavelength range of 600 to 700 nm.

In a case where light is incident on the imaging element 20a in the direction of the arrow, firstly, green light is mostly absorbed by the photoelectric conversion element 10a, but blue light and red light are transmitted through the photoelectric conversion element 10a. In a case where the light transmitted through the photoelectric conversion element 10a travels to the blue photoelectric conversion element 22, the blue light is mostly absorbed, but the red light is transmitted through the blue photoelectric conversion element 22. Thereafter, light transmitted through the blue photoelectric conversion element 22 is absorbed by the red photoelectric conversion element 24. As described above, in the imaging element 20a that is a laminated-type color separation imaging element, one pixel can be formed with three light receiving sections of green, blue, and red, and a large area of the light receiving section can be taken.

The configurations of the blue photoelectric conversion element 22 and the red photoelectric conversion element 24 are not particularly limited.

For example, the photoelectric conversion element having a configuration in which colors are separated by using silicon due to a difference in light absorption length may be used. Further specifically, for example, both the blue photoelectric conversion element 22 and the red photoelectric conversion element 24 may be made of silicon. In this case, as for light including blue light, green light, and red light that has entered the imaging element 20a in the direction of the arrow, the photoelectric conversion element 10a mostly receives the green light having the center wavelength, and the remaining blue light and red light are easily separated. The blue light and red light have different light absorption lengths for silicon (wavelength dependence of absorption coefficient for silicon), the blue light is easily absorbed near a surface of silicon, and the red light can penetrate deeper into the silicon. Based on such a difference in light absorption length, the blue light is mostly received by the blue photoelectric conversion element 22 existing in a shallower position, and the red light is mostly received by the red photoelectric conversion element 24 existing in a deeper position.

In addition, the blue photoelectric conversion element 22 and the red photoelectric conversion element 24 each may be a photoelectric conversion element (the blue photoelectric conversion element 22 or the red photoelectric conversion element 24) having a configuration including a conductive film, an organic photoelectric conversion film having a maximum absorption for blue light or red light, and a transparent conductive film in this order. For example, the blue photoelectric conversion element 22 may be the photoelectric conversion element according to the embodiment of the present invention in which the absorption wavelength is controlled so as to have a maximum absorption for the blue light. Similarly, the red photoelectric conversion element 24 may be the photoelectric conversion element according to the embodiment of the present invention in which the absorption wavelength is controlled so as to have a maximum absorption for the red light.

In FIG. 3, the photoelectric conversion element according to the embodiment of the present invention, the blue photoelectric conversion element, and the red photoelectric conversion element are arranged in this order from the light incident side, but the arrangement is not limited to this aspect, and may be another aspect. For example, the blue photoelectric conversion element, the photoelectric conversion element according to the embodiment of the present invention, and the red photoelectric conversion element may be arranged in this order from the light incident side.

In addition, the green photoelectric conversion element may be used as a photoelectric conversion element other than the photoelectric conversion element according to the embodiment of the present invention, and the blue photoelectric conversion element and/or the red photoelectric conversion element may be used as the photoelectric conversion element according to the embodiment of the present invention.

As described above, the configuration in which the photoelectric conversion elements of the three primary colors of blue, green, and red are laminated as the imaging element is described, but the configuration may be two layers (two colors) or four layers (four colors) or more.

For example, an aspect in which the photoelectric conversion element 10a according to the embodiment of the present invention may be arranged on the arrayed blue photoelectric conversion element 22 and red photoelectric conversion element 24 may be employed. As needed, a color filter that further absorbs light of a predetermined wavelength may be arranged on the light incident side.

The form of the imaging element is not limited to the above-described form and the form illustrated in FIG. 3 and may be other forms.

For example, an aspect in which the photoelectric conversion element according to the embodiment of the present invention, the blue photoelectric conversion element, and the red photoelectric conversion element may be arranged in the same plane position may be employed.

In addition, the photoelectric conversion element may be used as a single layer. For example, a configuration in which blue, red, and green color filters are arranged on the photoelectric conversion element 10a according to the embodiment of the present invention to separate colors may be employed.

The photoelectric conversion element according to the embodiment of the present invention is also preferably used as an optical sensor. The photoelectric conversion element may be used alone as the optical sensor, and the photoelectric conversion element may be used as a line sensor in which the photoelectric conversion elements are linearly arranged or as a two-dimensional sensor in which the photoelectric conversion elements are arranged in a plane shape.

<Material for Photoelectric Conversion Element>

The present invention also relates to a material for a photoelectric conversion element.

The material for a photoelectric conversion element is a material (a material for a photoelectric conversion element) used for manufacturing a photoelectric conversion element (preferably a photoelectric conversion element for an imaging element or an optical sensor) and containing a compound represented by Formula (3).

The compound represented by Formula (3) in the material for a photoelectric conversion element is the same as the compound represented by Formula (3) described above, and the preferable conditions are also the same.

Among these, the compound represented by Formula (3) in the material for a photoelectric conversion element is preferably the compound represented by Formula (4) described above.

It is preferable that the material for a photoelectric conversion element is preferably used for producing the photoelectric conversion film contained in the photoelectric conversion element.

A content of the compound represented by Formula (3) (preferably the compound represented by Formula (4)) contained in the material for a photoelectric conversion element is preferably 30% to 100% by mass, more preferably 70% to 100% by mass, and even more preferably 99% to 100% by mass with respect to the total mass of the material for a photoelectric conversion element.

The specific compound contained in the material for a photoelectric conversion element may be one kind alone or two or more kinds.

<Compound>

The present invention also relates to a compound.

The above-described compound is the compound represented by Formula (4) described above.

EXAMPLES

The present invention will be described in more detail based on Examples below. Materials, used amounts, ratios, treatment contents, treatment procedures, and the like described in the following Examples can be appropriately changed within the range that does not depart from the gist of the present invention. Therefore, the range of the present invention should not be limitatively interpreted by the following Examples.

[Compounds]

<Synthesis of Compound (D-1)>

An intermediate A was synthesized according to the methods described in paragraphs [0110] to [0120] of JP2015-149397A.

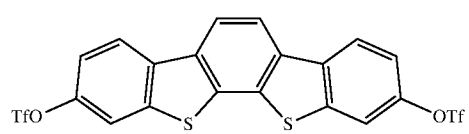

A

The intermediate A (2.00 g, 3.41 mmol), 4-biphenyl boronic acid (2.50 g, 12.6 mmol), [1,1'-bis (diphenylphosphino)ferrocene]dichloropalladium (II) dichloromethane adduct (0.141 g, 0.171 mmol), cesium carbonate (4.11 g, 12.6 mmol), cyclopentyl methyl ether (100 mL), and water (10 mL) were mixed in a 200 mL three-neck flask to obtain a mixed solution. The above-described mixed solution was repeatedly subjected to pressure reduction deairing treatment and nitrogen conversion treatment three times. The above-described mixed solution reacted at 100° C. for 9 hours under a nitrogen atmosphere, and thereafter, a solid precipitated from the above-described mixed solution was filtered off. The obtained crude product (solid) was heated in chlorobenzene at 140° C. for 1 hour and then filtered during heating, and the obtained solid was refined under reduced pressure by the sublimation method to obtain a compound (D-1).

The measurement result of the compound (D-1) by electrospray ionization mass spectrometry (ESI-MS) was as follows.

$$m/z = 594.15 \ (M^+)$$

<Synthesis of Compound (D-2)>

A compound (D-2) was obtained in the same manner as the compound (D-1), except that 4-biphenyl boronic acid in the synthesis of the compound (D-1) was changed to 4'-methyl-4-biphenyl boronic acid.

The measurement result of the compound (D-2) by ESI-MS was as follows.

$$m/z = 622.18 \ (M^+)$$

<Synthesis of Compound (D-3)>

A compound (D-3) was obtained in the same manner as the compound (D-1), except that 4-biphenyl boronic acid in the synthesis of the compound (D-1) was changed to 4-(4-biphenyl)phenyl boronic acid.

The measurement result of the compound (D-3) by ESI-MS was as follows.

$$m/z = 746.21 \ (M^+)$$

<Synthesis of Compound (D-4)>

A compound (D-4) was obtained in the same manner as the compound (D-1), except that 4-biphenyl boronic acid in the synthesis of the compound (D-1) was changed to 4'-methoxy-4-biphenyl boronic acid.

The measurement result of the compound (D-4) by ESI-MS was as follows.

$$m/z = 654.17 \ (M^+)$$

<Synthesis of Compound (D-5)>

A compound (D-5) was obtained in the same manner as the compound (D-1), except that 4-biphenyl boronic acid in the synthesis of the compound (D-1) was changed to 4'-chloro-4-biphenyl boronic acid.

The measurement result of the compound (D-5) by ESI-MS was as follows.

$$m/z = 662.07\ (M^+)$$

<Synthesis of Compound (D-6)>

A compound (D-6) was obtained in the same manner as in the synthesis of the compound (D-1), except that 4-biphenyl boronic acid in the synthesis of the compound (D-1) was changed to phenanthrene-2-yl boronic acid (synthesized by the method described in Journal of Fluorine Chemistry 2017, Vol. 203, pp. 173 to 184).

The measurement result of the compound (D-6) by ESI-MS was as follows.

$$m/z = 642.15\ (M^+)$$

<Synthesis of Compound (D-7)>

A compound (D-7) was obtained in the same manner as in the synthesis of the compound (D-1), except that 4-biphenyl boronic acid in the synthesis of the compound (D-1) was changed to 2-(4-(benzo[b]thiophene-2-yl)phenyl)-4,4,5,5-tetramethyl-1,3,2-dioxaborolane (synthesized by the method described a paragraph [0076] of WO2018/016465A).

The measurement result of the compound (D-7) by ESI-MS was as follows.

$$m/z = 706.09\ (M^+)$$

<Synthesis of Compound (D-8)>

A compound (D-8) was obtained in the same manner as the compound (D-1), except that 4-biphenyl boronic acid in the synthesis of the compound (D-1) was changed to phenylboronic acid.

The measurement result of the compound (D-8) by ESI-MS was as follows.

$$m/z = 442.08\ (M^+)$$

<Synthesis of Compound (D-9)>

A compound (D-9) was obtained in the same manner as in the synthesis of the compound (D-1), except that the intermediate A in the synthesis of the compound (D-1) was changed to a compound 30 described in EP2301926A.

The measurement result of the compound (D-9) by ESI-MS was as follows.

$$m/z = 594.15\ (M^+)$$

<Synthesis of Compound (D-10)>

3-methoxyphenylthiol in a paragraph [0113] of JP2015-149397A was changed to 7-methoxynaphthalene-2-thiol to synthesize an intermediate B based on the method described in paragraphs [0110] to [0120] of JP2015-149397A.

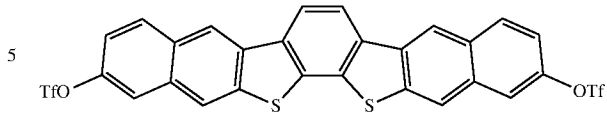

B

A compound (D-10) was obtained in the same manner as in the synthesis of the compound (D-8), except that the intermediate A in the synthesis of the compound (D-8) was changed to the intermediate B.

The measurement result of the compound (D-10) by ESI-MS was as follows.

$$m/z = 542.12\ (M^+)$$

<Synthesis of Compound (D-11)>

0.42 g (3.41 mmol) of phenyl boronic acid in the synthesis of the compound (D-8) was used to carry out a reaction in a flask in the same manner as in the synthesis of the compound (D-8). After confirming the disappearance of the intermediate A, 1-bromobutane (0.918 g, 6.8 mmol), allylpalladium (II) chloride (dimer) (121 mg, 0.341 mmol), tricyclohexylphosphin (191 mg, 0.682 mmol), and tetramethylammonium fluoride (1.15 g, 4.5 mmol) were added in the flask to continuously carry out a reaction and post-treatment in the same manner as in the synthesis of the compound (D-1), and as a result, a compound (D-11) was obtained.

The measurement result of the compound (D-11) by ESI-MS was as follows.

$$m/z = 422.12\ (M^+)$$

<Synthesis of Compound (D-12)>

A compound (D-12) was obtained by converting R to 4-biphenyl and carrying out a synthesis according to the method described in Scheme 1 in the paper of Beilstein Journal of Organic Chemistry 2016, Volume 12, pp. 805 to 812.

The measurement result of the compound (D-12) by ESI-MS was as follows.

$$m/z = 562.19\ (M^+)$$

<Synthesis of Compound (R-1)>

A compound (R-1) is a compound 1-169 in WO2009/148062A, and synthesized according to the method described in WO2009/148062A.

<Synthesis of Compound (R-2)>

A compound (R-2) is a compound 1054 in JP2010-59147A, and was synthesized according to the method described in JP2010-59147A.

Hereinbelow, the compounds (D-1) to (D-12) that are specific compounds, and the compounds (R-1) and (R-2) for comparison are illustrated.

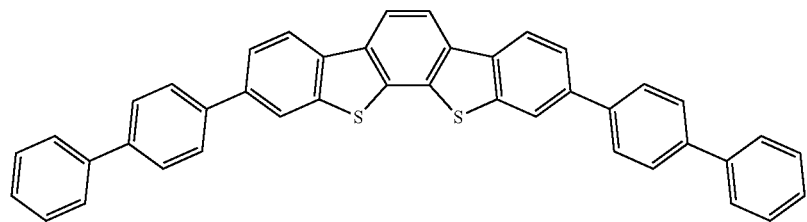
D-1
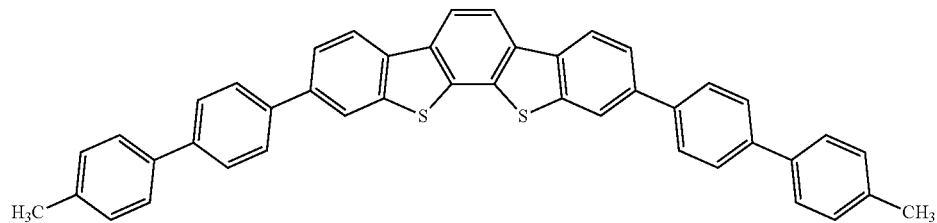
D-2
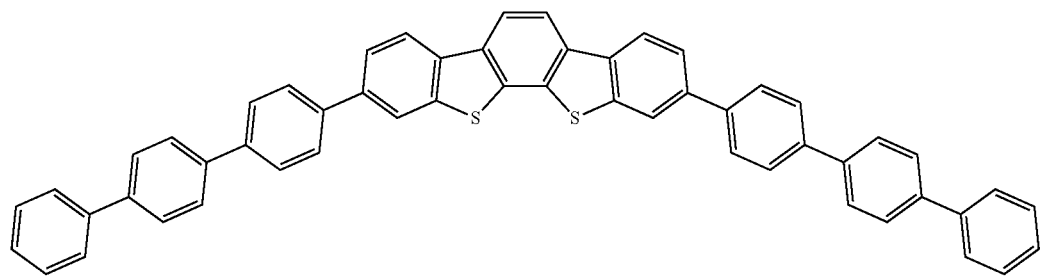
D-3
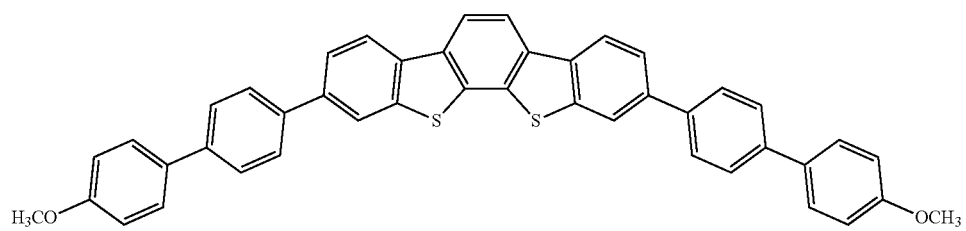
D-4
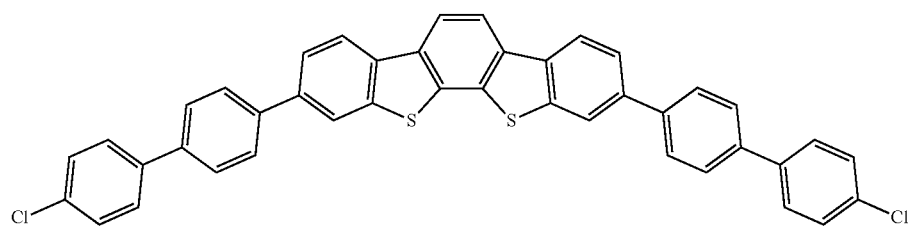
D-5
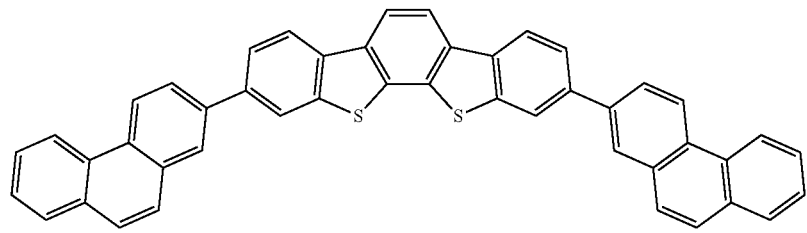
D-6

-continued
D-7
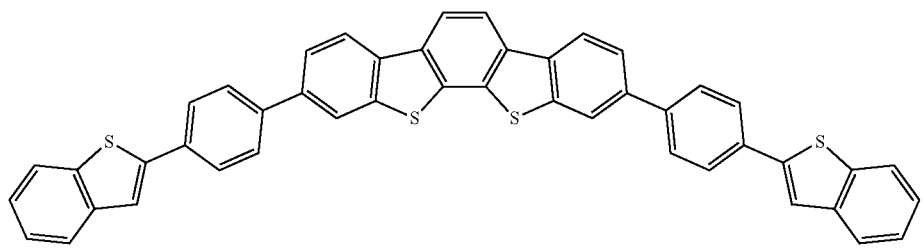
D-8
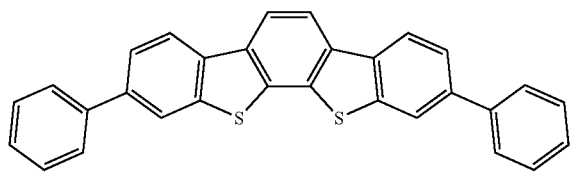
D-9
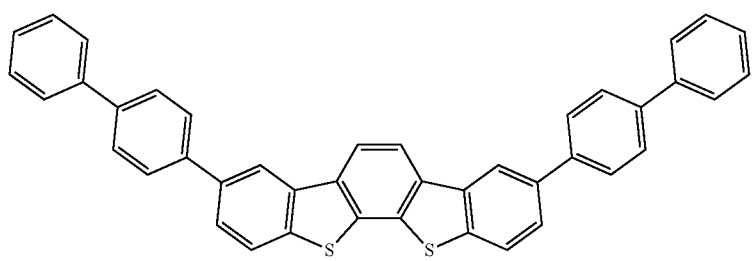
D-10
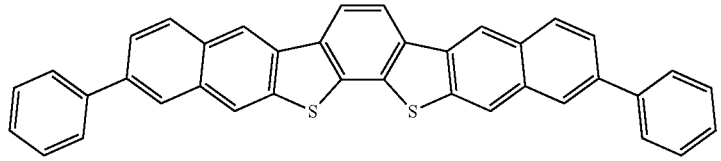
D-11
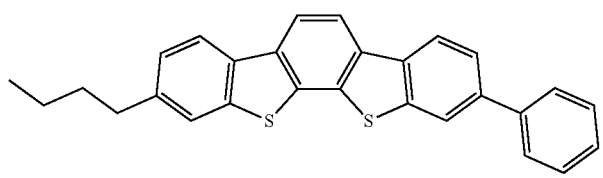
D-12
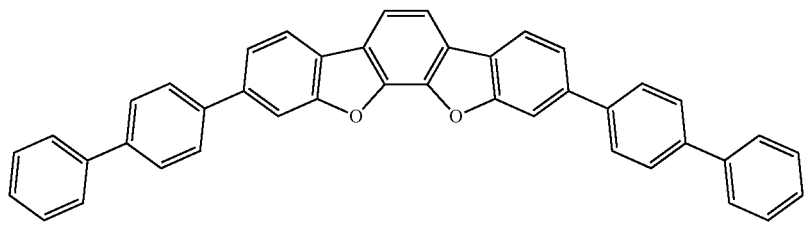
R-1
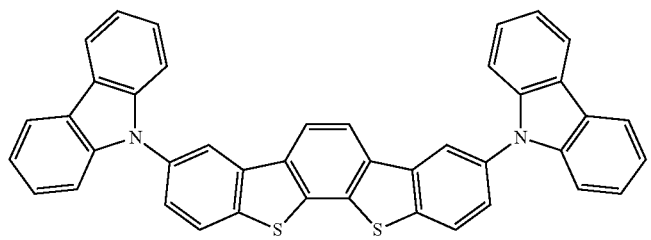

-continued

R-2

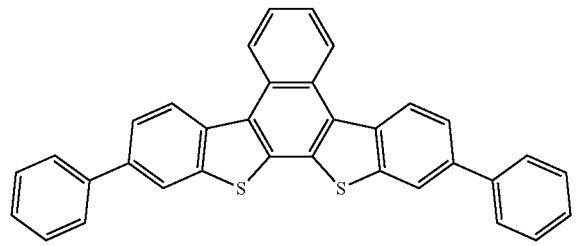

Each of LUMO values of the compounds (D-1) to (D-12), (R-1) and (R-2), and a fullerene (C60) was calculated by B3LYP/6-31G (d) using Gaussian '09 (software manufactured by Gaussian, Inc.). Values of the reciprocal of the obtained LUMO values were adopted as electron affinity values of the compounds.

As a result, it was confirmed that the electron affinity of the fullerene (C60) was larger than the electron affinity of any of the compounds (D-1) to (D-12), and (R-1) and (R-2). That is, it was confirmed that the fullerene (C60) corresponds to an n-type semiconductor material in relation to the compounds (D-1) to (D-12), (R-1), and (R-2).

[Tests]

Examples and Comparative Examples: Production of Photoelectric Conversion Element The photoelectric conversion element of the form illustrated in FIG. 2 was produced using the obtained compounds. Here, the photoelectric conversion element includes a lower electrode 11, an electron blocking film 16A, a photoelectric conversion film 12, a positive hole blocking film 16B, and an upper electrode 15.

Specifically, an amorphous ITO was formed into a film on a glass substrate by a sputtering method to form the lower electrode 11 (thickness: 30 nm). Furthermore, a compound (B-1) described below was formed into a film on the lower electrode 11 by a vacuum thermal vapor deposition method to form the electron blocking film 16A (thickness: 10 nm).

Furthermore, the compound (D-1) and the fullerene (C60) were set to a vapor deposition rate of 2.0 Å/sec and subjected to co-vapor deposition by a vacuum evaporation method to be 150 nm and 150 nm respectively, in terms of a single layer, on the electron blocking film 16A to be formed into a film in a state where the temperature of the substrate was controlled to 25° C., and the photoelectric conversion film 12 having a bulk hetero structure of 300 nm was formed (a step of forming a photoelectric conversion film).

Furthermore, a compound (B-2) described below was formed into a film on the photoelectric conversion film 12 to form the positive hole blocking film 16B (thickness: 10 nm).

Furthermore, amorphous ITO was formed into a film on the positive hole blocking film 16B by a sputtering method to form the upper electrode 15 (the transparent conductive film) (thickness: 10 nm). A SiO film was formed as a sealing layer on the upper electrode 15 by a vacuum evaporation method, and thereafter, an aluminum oxide ($Al_2O_3$) layer was formed thereon by an atomic layer chemical vapor deposition (ALCVD) method to produce a photoelectric conversion element, and this element was denoted by an element ($A_{D-1}$).

B-1

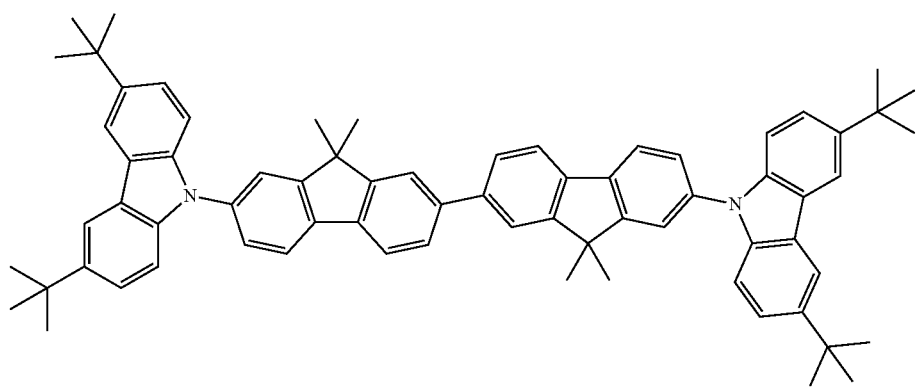

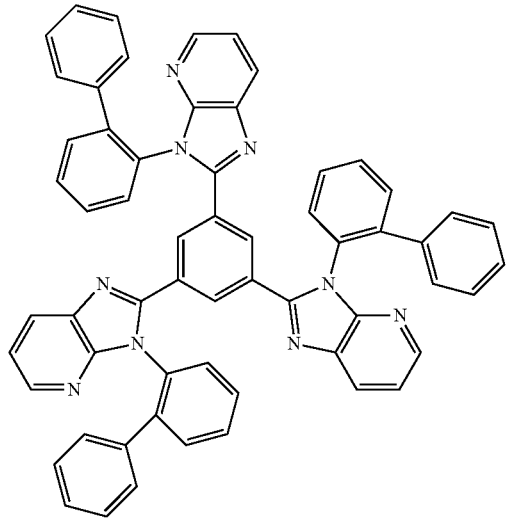

B-2

By using each of the compounds (D-2) to (D-12), (R-1), or (R-2) instead of the compound (D-1), photoelectric conversion elements were produced in the same manner to obtain elements ($A_{D-2}$) to ($A_{D-12}$), ($A_{R-1}$), and ($A_{R-2}$).

<Evaluation of Photoelectric Conversion Efficiency>

The drive of each of the obtained elements was confirmed. A voltage was applied to each element to have an electric field strength of $2.0 \times 10^5$ V/cm. Thereafter, light was emitted from the upper electrode (transparent conductive film) side to evaluate the photoelectric conversion efficiency (external quantum efficiency) at 400 nm. The external quantum efficiency was measured using a constant energy quantum efficiency measuring device manufactured by Optel Co., Ltd. The amount of light emitted was 50 μW/cm².

An external quantum efficiency of 70% or more is denoted by "AA", 60% or more and less than 70% is denoted by "A", 50% or more and less than 60% is denoted by "B", 40% or more and less than 50% is denoted by "C", and less than 40% is denoted by "D", to perform the evaluation.

Practically, "AA", "A", and "B" are preferable, "AA" and "A" are more preferable, and "AA" is even more preferable.

<Evaluation of Responsiveness after Heating Over Time>

Each of the obtained elements was used to perform the following evaluation of responsiveness after heating over time.

Specifically, each element (photoelectric conversion element) was heat-treated in a glove box at 160° C. for 2 hours and cooled to room temperature (25° C.). Thereafter, a voltage was applied to each element to have an electric field strength of $2.0 \times 10^5$ V/cm. Thereafter, light emitting diodes (LEDs) were turned on momentarily to emit light from the upper electrode (transparent conductive film) side, a photo current at that time was measured with an oscilloscope, and a rise time of signal intensity from 0% to 97% was calculated. The rise time of the element (element ($A_{R-1}$)) of Comparative Example 1 was denoted by 1, and a relative value of the rise time with respect to the element to be evaluated was obtained to evaluate responsiveness of each element. The results are illustrated in Table 1.

The relative value of the rise time of less than 0.1 was denoted by "AA", 0.1 or more and less than 0.3 was denoted by "A", 0.3 or more and less than 1 was denoted by "B", 1 or more and less than 3 was denoted by "C", and 3 or more was denoted by "D", with respect to Comparative Example 1. The results are illustrated in Table 1.

Practically, "AA", "A", and "B" are preferable, "AA" and "A" are more preferable, and "AA" is even more preferable.

The results of the tests conducted using the photoelectric conversion elements produced by using each compound are illustrated in Table 1 below.

In Table, the column of "Compound" indicates the type of the compounds used in the production of the elements that have been evaluated.

In Table, the column "Formula (2)" indicates whether or not the specific compound used corresponds to the compound represented by Formula (2). A case where this requirement was satisfied was described as "A", and a case where this requirement was not satisfied was described as "B".

In Table, the column of "$X^1/X^2=S$" indicates whether or not $X^1$ and $X^2$ are each sulfur atoms in a case where each specific compound used was applied to Formula (1). A case where this requirement was satisfied was described as "A", and a case where this requirement was not satisfied was described as "B".

In Table, the column of "$R^2/R^9$ (1)" indicates whether or not $R^2$ and $R^9$ each are a polycyclic aryl group which may have a substituent, a polycyclic heteroaryl group which may have a substituent, or a group represented by Formula (W-1) in a case where each specific compound used was applied to Formula (W-1). A case where this requirement was satisfied was described as "A", and a case where this requirement was not satisfied was described as "B".

In Table, the column of "$R^2/R^9$ (2)" indicates whether or not $R^2$ and $R^9$ each are a polycyclic aryl group with 3 or more rings which may have a substituent, a polycyclic heteroaryl group which may have a substituent, or a group represented by Formula (W-2) in a case where each specific compound used was applied to Formula (W-1). A case where this requirement was satisfied was described as "A", and a case where this requirement was not satisfied was described as "B".

TABLE 1

| | | | Compound characteristics | | | | Evaluation | |
|---|---|---|---|---|---|---|---|---|
| | | | | | | | Photoelectric | Responsiveness |
| | Element | Compound | Formula (2) | $X^1/X^2$ = S | $R^2/R^9$ (1) | $R^2/R^9$ (2) | conversion efficiency | after heating over time |
| Example 1 | $A_{D-1}$ | D-1 | A | A | A | A | AA | AA |
| Example 2 | $A_{D-2}$ | D-2 | A | A | A | B | AA | A |
| Example 3 | $A_{D-3}$ | D-3 | A | A | A | A | AA | AA |
| Example 4 | $A_{D-4}$ | D-4 | A | A | A | B | AA | A |
| Example 5 | $A_{D-5}$ | D-5 | A | A | A | A | AA | AA |
| Example 6 | $A_{D-6}$ | D-6 | A | A | A | A | AA | AA |
| Example 7 | $A_{D-7}$ | D-7 | A | A | A | A | AA | AA |
| Example 8 | $A_{D-8}$ | D-8 | A | A | B | B | B | A |
| Example 9 | $A_{D-9}$ | D-9 | A | A | B | B | B | A |
| Example 10 | $A_{D-10}$ | D-10 | B | A | B | B | B | B |
| Example 11 | $A_{D-11}$ | D-11 | B | A | B | B | B | B |
| Example 12 | $A_{D-12}$ | D-12 | A | B | A | A | A | A |
| Comparative Example 1 | $A_{R-1}$ | R-1 | — | — | — | — | D | C |
| Comparative Example 2 | $A_{R-2}$ | R-2 | — | — | — | — | C | D |

From the results illustrated in Table 1, it was confirmed that the photoelectric conversion element according to the embodiment of the present invention using the specific compound for the photoelectric conversion film was excellent in the photoelectric conversion efficiency and the responsiveness after heating over time.

By contrary, in a case where the compounds (R-1) or (R-2) different from the specific compound was used, the photoelectric conversion efficiency and the responsiveness of the obtained photoelectric conversion element after heating over time were inferior in comparison with the photoelectric conversion element according to the embodiment of the present invention.

It was confirmed that the effect of the present invention is more excellent in the case where the specific compound was the compound represented by Formula (2) (see the comparison between Examples 10 and 11, and other Examples, and the like).

It was confirmed that the effect of the present invention is more excellent in the case where $X^1$ and $X^2$ each represent a sulfur atom in the case where the specific compound was applied to Formula (1) (see the comparison between Examples 1 and 12, and other Examples, and the like).

It was confirmed that the effect of the present invention is more excellent in the case where $R^2$ and $R^9$ each represent a polycyclic aryl group which may have a substituent, a polycyclic heteroaryl group which may have a substituent, or a group represented by Formula (W-1) in a case where each specific compound used was applied to Formula (1) (see the comparison between Examples 1 to 7, and 12, and other Examples, and the like).

It was confirmed that the effect of the present invention is more excellent in the case where $R^2$ and $R^9$ each are a polycyclic aryl group with 3 or more rings which may have a substituent, a polycyclic heteroaryl group which may have a substituent, or a group represented by Formula (W-2) in a case where the specific compound used was applied to Formula (1) (see the comparison between Examples 1, 3, 5, 6 and Examples 2 and 4 (the comparison between Examples using the specific compounds satisfying all the requirements of individual columns except for the column of "$R^2/R^9$ (2)" in Table), and the like).

EXPLANATION OF REFERENCES 10a and 10b: Photoelectric conversion element
11: Conductive film (lower electrode)
12: Photoelectric conversion film
15: Transparent conductive film (upper electrode)
16A: Electron blocking film
16B: Positive hole blocking film
20a: Imaging element
22: Blue photoelectric conversion element
24: Red photoelectric conversion element

What is claimed is:
1. A photoelectric conversion element comprising, in the following order:
a conductive film;
a photoelectric conversion film; and
a transparent conductive film,
wherein the photoelectric conversion film contains a compound represented by Formula (1) and an n-type semiconductor material,

(1)

in Formula (1), $C^1$, $C^3$, $C^8$, and $C^{10}$ each represent a carbon atom,
$X^1$ and $X^2$ each independently represent a sulfur atom, an oxygen atom, a selenium atom, a tellurium atom, $CR^{c1}R^{c2}$, $SiR^{c3}R^{c4}$, or $NR^{c5}$,
$R^{c1}$ to $R^{c5}$ each independently represent a hydrogen atom or a substituent,
p and q each independently represent an integer of 0 to 2,
$R^5$ and $R^6$ each independently represent a hydrogen atom or a substituent, and $R^1$, $R^3$, $R^4$, $R^7$, $R^8$, $R^{10}$, $R^{a1}$, $R^{a2}$, $R^{b1}$, and $R^{b2}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, where, in a case where $R^1$ is a heteroaryl group with or without a substituent, wherein an atom directly bonded to $C^1$ in the $R^1$ with the substituent is a carbon atom, in a case where $R^3$ is a heteroaryl group with or without a substituent, wherein an atom directly bonded to $C^3$ in the $R^3$ with the substituent is a carbon atom, in a case where $R^8$ is a heteroaryl group with or without a substituent, wherein an atom directly bonded to $C^8$ in the $R^8$ with the substituent is a carbon atom, and in a case where $R^{10}$ is a heteroaryl group with or without a substituent, wherein an atom directly bonded to $C^{10}$ in the $R^{10}$ with the substituent is a carbon atom, wherein $R^2$ and $R^9$ each independently represent a polycyclic aryl group with or without a substituent, a polycyclic heteroaryl group with or without a substituent, or a group represented by Formula (W-1),

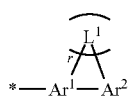
(W-1)

in Formula (W-1), * represents a bonding position, $Ar^1$ represents a monocyclic aromatic ring group with or without a substituent, $Ar^2$ represents an aromatic ring group with or without a substituent, r represents 0 or 1, $L^1$ represents a sulfur atom, an oxygen atom, a selenium atom, $SiR^{w1}R^{w2}$, $NR^{w3}$, or $CR^{w4}R^{w5}$, and $R^{w1}$ to $R^{w5}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, where, in a case where r represents 0, $L^1$ does not exist, and $Ar^1$ and $Ar^2$ are connected only by a single bond specified in Formula (W-1).

2. The photoelectric conversion element according to claim 1, wherein $X^1$ and $X^2$ each independently represent a sulfur atom, an oxygen atom, or a selenium atom.

3. The photoelectric conversion element according to claim 1, wherein at least one of $R^1$ to $R^{10}$, $R^{a1}$, $R^{a2}$, $R^{b1}$, or $R^{b2}$ represents an aryl group with or without a substituent or a heteroaryl group with or without a substituent.

4. The photoelectric conversion element according to claim 1, wherein the compound represented by Formula (1) is a compound represented by Formula (2),

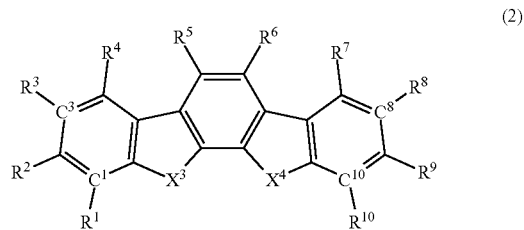
(2)

in Formula (2), $C^1$, $C^3$, $C^8$, and $C^{10}$ each represent a carbon atom, $X^3$ and $X^4$ each independently represent a sulfur atom or an oxygen atom, $R^5$ and $R^6$ each independently represent a hydrogen atom or a substituent, $R^1$, $R^3$, $R^4$, $R^7$, $R^8$, $R^{10}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, and where, in a case where $R^1$ is a heteroaryl group with or without a substituent, wherein an atom directly bonded to $C^1$ in the $R^1$ with the substituent is a carbon atom, in a case where $R^3$ is a heteroaryl group with or without a substituent, wherein an atom directly bonded to $C^3$ in the $R^3$ with the substituent is a carbon atom, in a case where $R^8$ is a heteroaryl group with or without a substituent, wherein an atom directly bonded to $C^8$ in the $R^8$ with the substituent is a carbon atom, and in a case where $R^{10}$ is a heteroaryl group with or without a substituent, wherein an atom directly bonded to $C^{10}$ in the $R^{10}$ with the substituent is a carbon atom.

5. The photoelectric conversion element according to claim 4, wherein $X^3$ and $X^4$ each represent a sulfur atom.

6. The photoelectric conversion element according to claim 1, wherein $R^2$ and $R^9$ each independently represent a polycyclic aryl group with 3 or more rings, with or without a substituent, a polycyclic heteroaryl group with or without a substituent, or a group represented by Formula (W-2),

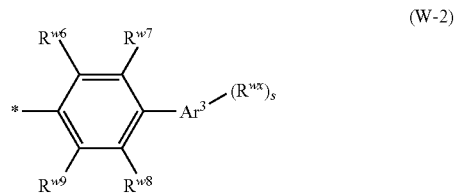
(W-2)

in Formula (W-2), * represents a bonding position, $R^{w6}$ to $R^{w9}$ each independently represent a hydrogen atom, a halogen atom, an alkylthio group with or without a substituent, an aryl group with or without a group selected from the group consisting of a halogen atom, an alkoxy group, and an alkylthio group as a substituent, or a heteroaryl group with or without a group selected from the group consisting of a halogen atom, an alkoxy group, and an alkylthio group as a substituent, Ar³ represents a benzene ring group or a polycyclic aromatic heterocyclic group, $R^{wx}$ represents a halogen atom, an alkylthio group with or without a substituent, an aryl group with or without a group selected from the group consisting of a halogen atom, an alkoxy group, and an alkylthio group as a substituent, or a heteroaryl group with or without a group selected from the group consisting of a halogen atom, an alkoxy group, and an alkylthio group as a substituent, and s represents an integer of 0 or more.

7. The photoelectric conversion element according to claim 1, wherein the compound represented by Formula (1) has a molecular weight of 400 to 900.

8. The photoelectric conversion element according to claim 1, wherein the photoelectric conversion film has a bulk hetero structure formed in a state where the compound represented by Formula (1) and the n-type semiconductor material are mixed with each other.

9. The photoelectric conversion element according to claim 1, further comprising one or more interlayers between the conductive film and the transparent conductive film, in addition to the photoelectric conversion film.

10. The photoelectric conversion element according to claim 1, wherein the n-type semiconductor material includes fullerenes selected from the group consisting of a fullerene and a derivative thereof.

11. An imaging element comprising the photoelectric conversion element according to claim 1.

12. An optical sensor comprising the photoelectric conversion element according to claim 1.

13. The photoelectric conversion element according to claim 2, wherein at least one of $R^1$, $R^3$, $R^4$, $R^7$, $R^8$, $R^{10}$, $R^{a1}$, $R^{a2}$, $R^{b1}$, or $R^{b2}$ represents an aryl group with or without a substituent or a heteroaryl group with or without a substituent.

14. The photoelectric conversion element according to claim 2, wherein the compound represented by Formula (1) is a compound represented by Formula (2),

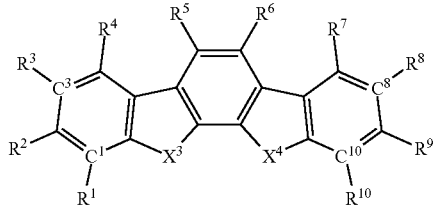

(2)

in Formula (2), $C^1$, $C^3$, $C^8$, and $C^{10}$ each represent a carbon atom, $X^3$ and $X^4$ each independently represent a sulfur atom or an oxygen atom, $R^5$ and $R^6$ each independently represent a hydrogen atom or a substituent, $R^1$, $R^3$, $R^4$, $R^7$, $R^8$, $R^{10}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, and where, in a case where $R^1$ is a heteroaryl group with or without a substituent, wherein an atom directly bonded to $C^1$ in the $R^1$ with the substituent is a carbon atom, in a case where $R^3$ is a heteroaryl group with or without a substituent, wherein an atom directly bonded to $C^3$ in the $R^3$ with the substituent is a carbon atom, in a case where $R^8$ is a heteroaryl group with or without a substituent, wherein an atom directly bonded to $C^8$ in the $R^8$ with the substituent is a carbon atom, and in a case where $R^{10}$ is a heteroaryl group with or without a substituent, wherein an atom directly bonded to $C^{10}$ in the $R^{10}$ with the substituent is a carbon atom.

15. The photoelectric conversion element according to claim 14, wherein $X^3$ and $X^4$ each represent a sulfur atom.

16. The photoelectric conversion element according to claim 2, wherein $R^2$ and $R^9$ each independently represent a polycyclic aryl group with 3 or more rings, with or without a substituent, a polycyclic heteroaryl group with or without a substituent, or a group represented by Formula (W-2),

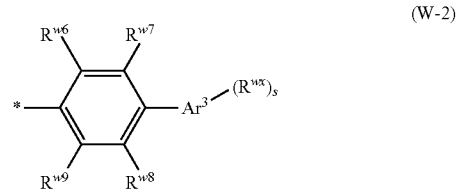

(W-2)

in Formula (W-2), * represents a bonding position, $R^{w6}$ to $R^{w9}$ each independently represent a hydrogen atom, a halogen atom, an alkylthio group with or without a substituent, an aryl group with or without a group selected from the group consisting of a halogen atom, an alkoxy group, and an alkylthio group as a substituent, or a heteroaryl group with or without a group selected from the group consisting of a halogen atom, an alkoxy group, and an alkylthio group as a substituent, Ar³ represents a benzene ring group or a polycyclic aromatic heterocyclic group, $R^{wx}$ represents a halogen atom, an alkylthio group with or without a substituent, an aryl group with or without a group selected from the group consisting of a halogen atom, an alkoxy group, and an alkylthio group as a substituent, or a heteroaryl group with or without a group selected from the group consisting of a halogen atom, an alkoxy group, and an alkylthio group as a substituent, and s represents an integer of 0 or more.

17. A material for a photoelectric conversion element comprising a compound represented by Formula (3),

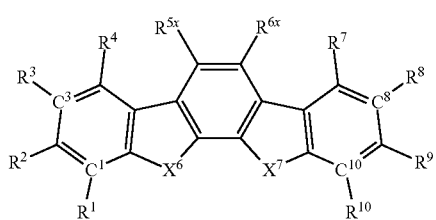

(3)

in Formula (3), $C^1$, $C^3$, $C^8$, and $C^{10}$ each represent a carbon atom, $X^3$ and $X^4$ each independently represent a sulfur atom or an oxygen atom, $R^1$, $R^3$, $R^4$, $R^7$, $R^8$, $R^{10}$, $R^{5x}$, and $R^{6x}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, and where, in a case where $R^1$ is a heteroaryl group with or without a substituent, wherein an atom directly bonded to $C^1$ in the $R^1$ with the substituent is a carbon atom, in a case where $R^3$ is a heteroaryl group with or without a substituent, wherein an atom directly bonded to $C^3$ in the $R^3$ with the substituent, is a carbon atom, in a case where $R^8$ is a heteroaryl group with or without a substituent, wherein an atom directly bonded to $C^8$ in the $R^8$ with the substituent is a carbon atom, and in a case where $R^{10}$ is a heteroaryl group with or without a substituent, an atom directly bonded to $C^{10}$ in the $R^{10}$ with the substituent is a carbon atom, wherein $R^2$ and $R^9$ each independently represent a polycyclic aryl group with or without a substituent, a polycyclic heteroaryl group with or without a substituent, or a group represented by Formula (W-1),

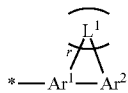

(W-1)

in Formula (W-1), * represents a bonding position, $Ar^1$ represents a monocyclic aromatic ring group with or without a substituent, $Ar^2$ represents an aromatic ring group with or without a substituent, r represents 0 or 1, $L^1$ represents a sulfur atom, an oxygen atom, a selenium atom, $SiR^{w1}R^{w2}$, $NR^{w3}$, or $CR^{w4}R^{w5}$, and $R^{w1}$ to $R^{w5}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, where, in a case where r represents 0, $L^1$ does not exist, and $Ar^1$ and $Ar^2$ are connected only by a single bond specified in Formula (W-1).

18. A compound represented by Formula (4),

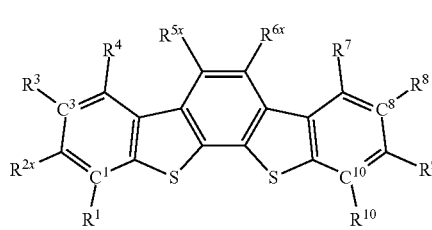

(4)

in Formula (4), $C^1$, $C^3$, $C^8$, and $C^{10}$ each represent a carbon atom, $R^1$, $R^3$, $R^4$, $R^7$, $R^8$, $R^{10}$, $R^{5x}$, and $R^{6x}$ each independently represent a hydrogen atom, a halogen atom, an alkyl group with or without a substituent, an alkoxy group with or without a substituent, an alkylthio group with or without a substituent, a silyl group with or without a substituent, an alkenyl group with or without a substituent, an alkynyl group with or without a substituent, an aryl group with or without a substituent, or a heteroaryl group with or without a substituent, where, in a case where $R^1$ is a heteroaryl group with or without a substituent, wherein an atom directly bonded to $C^1$ in the $R^1$ with the substituent is a carbon atom, in a case where $R^3$ is a heteroaryl group with or without a substituent, wherein an atom directly bonded to $C^3$ in the $R^3$ with the substituent is a carbon atom, in a case where $R^8$ is a heteroaryl group with or without a substituent, wherein an atom directly bonded to $C^8$ in the $R^8$ with the substituent is a carbon atom, and in a case where $R^{10}$ is a heteroaryl group with or without a substituent, wherein an atom directly bonded to $C^{10}$ in the $R^{10}$ with the substituent is a carbon atom, $R^{2x}$ and $R^{9x}$ each independently represent a polycyclic aryl group with 3 or more rings, with or without a substituent, a polycyclic heteroaryl group with or without a substituent, or a group represented by Formula (W-2),

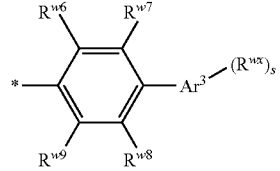

(W-2)

in Formula (W-2), * represents a bonding position, $R^{w6}$ to $R^{w9}$ each independently represent a hydrogen atom, a halogen atom, an alkylthio group with or without a substituent, an aryl group with or without a group selected from the group consisting of a halogen atom, an alkoxy group, and an alkylthio group as a substituent, or a heteroaryl group with or without a group selected from the group consisting of a halogen atom, an alkoxy group, and an alkylthio group as a substituent, Ar$^3$ represents a benzene ring group or a polycyclic aromatic heterocyclic group, R$^{wx}$ represents a halogen atom, an alkylthio group with or without a substituent, an aryl group with or without a group selected from the group consisting of a halogen atom, an alkoxy group, and an alkylthio group as a substituent, or a heteroaryl group with or without a group selected from the group consisting of a halogen atom, an alkoxy group, and an alkylthio group as a substituent, and s represents an integer of 0 or more.

\* \* \* \* \*